United States Patent
Lukač et al.

(10) Patent No.: US 12,226,152 B2
(45) Date of Patent: Feb. 18, 2025

(54) NON-ABLATIVE RESURFACING OF SOFT TISSUES

(71) Applicant: Fotona d.o.o., Ljubljana (SI)

(72) Inventors: Matjaz Lukač, Ljubljana (SI); Nejc Lukač, Ljubljana (SI); Blaz Tasic Muc, Kamnik (SI); Anže Zorman, Logatec (SI); Tadej Perhavec, Sežana (SI)

(73) Assignee: Fotona d.o.o., Ljubljana (SI)

( * ) Notice: Subject to any disclaimer, the term of this patent is extended or adjusted under 35 U.S.C. 154(b) by 380 days.

(21) Appl. No.: 17/674,550

(22) Filed: Feb. 17, 2022

(65) Prior Publication Data
US 2022/0266055 A1    Aug. 25, 2022

(30) Foreign Application Priority Data
Feb. 18, 2021 (EP) .................................. 21157917

(51) Int. Cl.
*A61N 5/06* (2006.01)
*A61B 18/20* (2006.01)
*A61N 5/067* (2006.01)
*H01S 3/16* (2006.01)

(52) U.S. Cl.
CPC .......... *A61B 18/203* (2013.01); *A61N 5/0616* (2013.01); *A61N 5/067* (2021.08); *H01S 3/1608* (2013.01); *H01S 3/1643* (2013.01); *A61N 2005/0626* (2013.01)

(58) Field of Classification Search
CPC ........ A61B 18/203; A61B 2018/00452; A61B 2018/00714; A61B 2018/20351; A61N 5/0616; A61N 5/067; A61N 2005/0626; A61N 5/0625; H01S 3/1608; H01S 3/1643
See application file for complete search history.

(56) References Cited

U.S. PATENT DOCUMENTS

| 5,643,334 | A | 7/1997 | Eckhouse et al. |
| 2008/0221649 | A1 | 9/2008 | Echague et al. |
| 2009/0254068 | A1* | 10/2009 | Karni ............... A61B 18/20 606/9 |
| 2014/0155962 | A1 | 6/2014 | Deroberts |
| 2016/0175612 | A1 | 6/2016 | Kazic et al. |
| 2020/0170704 | A1 | 6/2020 | Lukac et al. |

FOREIGN PATENT DOCUMENTS

EP    3569287 A1    11/2019

OTHER PUBLICATIONS

European Search Report issued for corresponding EP Application No. 21157917.2, dated Aug. 4, 2021.

* cited by examiner

*Primary Examiner* — Scott M. Getzow
(74) *Attorney, Agent, or Firm* — Renner, Otto, Boisselle & Sklar, LLP

(57) ABSTRACT

The present disclosure relates to a method and an apparatus for generating a laser pulse sequence for application to a predetermined target tissue. Means are provided for setting a cumulative fluence $F_s$ of the laser pulse sequence. Means are provided for determining a duration of the laser pulse sequence as a function of the cumulative fluence $F_s$ such that the predetermined target tissue is heated to a final temperature that is within a predetermined range.

15 Claims, 8 Drawing Sheets

NON-ABLATIVE RESURFACING OF SOFT TISSUES

Figure 1A:
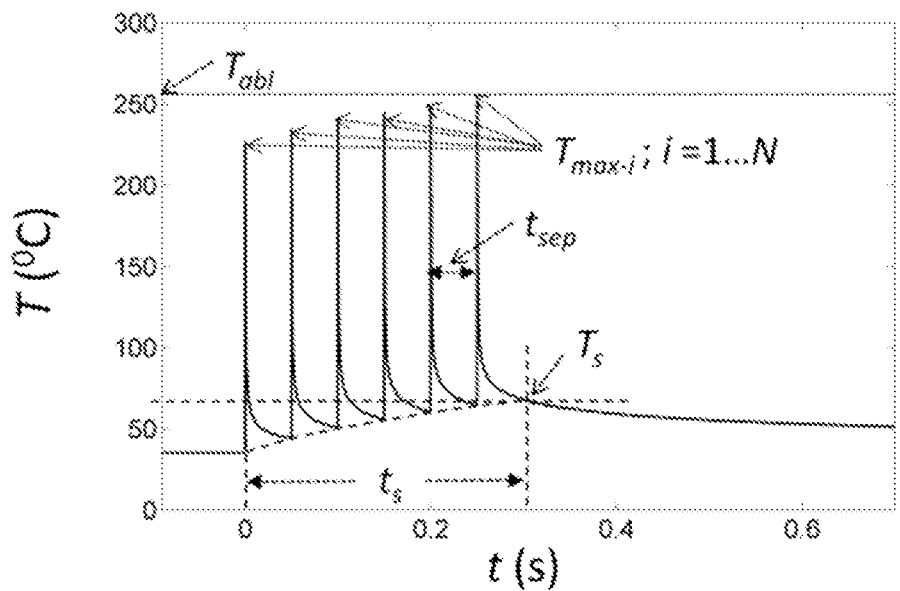

This application claims priority of European Patent Application No. 21157917.2 filed Feb. 18, 2021, the entire disclosure of which is hereby incorporated by reference.

1. TECHNICAL FIELD

The present invention generally relates to an apparatus, a method and a computer program for generating a laser pulse sequence. The laser pulse sequence may be adapted to be applied to a predetermined target tissue, e.g. for tissue regeneration, skin regeneration, skin tightening, wrinkle removal, hair regrowth, for treating urinary incontinence, fecal incontinence, erectile dysfunction and/or snoring related sleep disorders.

2. BACKGROUND

Laser pulses and sequences of laser pulses have long been used for various types of procedures adapted to manipulate tissue, such as cutaneous or mucosal tissue. Procedures have ranged from purely cosmetic or aesthetic applications such as skin tightening which aim at removing wrinkles to medical applications such as treating snoring related sleep disorders, urinary incontinence, fecal incontinence, erectile dysfunction, hair regrowth etc. For example, US patent application US 2020/0170704 A1 discloses various applications.

Of specific interest have recently been pulses or pulse sequences with limited fluence and of relatively short duration which are non-ablative and thus allow for safe applications without excessive healing times of the treated tissue. Such pulses are for example described in European patent application EP 3 569 287 A1.

However, the approaches known so far still do not always provide optimum results.

There is therefore a need to further optimize the known apparatus or methods of generating laser pulse sequences.

3. SUMMARY OF THE INVENTION

In an aspect, this need is at least in part met by an apparatus for generating a laser pulse sequence for application to a predetermined target tissue, e.g. for tissue regeneration (e.g. tissue regeneration, skin regeneration, skin tightening, etc.). The apparatus may comprise means for setting a cumulative fluence $F_s$ of the laser pulse sequence. The apparatus may further comprise means for determining a duration of the laser pulse sequence as a function of the cumulative fluence $F_s$ such that the predetermined target tissue is heated to a final temperature (increase) that is within a predetermined range.

As will be outlined in further detail below, the inventors of the present invention have determined via various experiments that the pain experienced by a patient depends predominantly on the final temperature after a pulse sequence has been delivered, but not on the (short-term) temperature peaks caused by individual pulses and their transients. In fact, the quickly decaying temperature transients may cause, on short time scales, tissue temperatures above 100° C. and even up to the tissue boiling point of about 250° C. without causing significant pain, if the long term baseline tissue temperature caused by the pulse sequence remains below a certain threshold.

Another important aspect is that the final (baseline) temperature (increase) after an application of a laser pulse sequence directed at the same tissue of a predetermined type (e.g. each pulse having the same flat beam or standard Gaussian pulse intensity distribution) essentially depends only on the cumulative fluence of the sequence of laser pulses and the duration of the laser pulse sequence. Hence, a corresponding temperature model can be established, linking cumulative fluence and duration of the laser pulse sequence with a final temperature (increase). Hence, from a given set of cumulative fluence and pulse duration, the final temperature (increase) can be determined, e.g. based on the temperature model.

Therefore, if, e.g. a physician or a cosmetician, sets a predetermined cumulative pulse fluence (e.g. via a user interface), the duration of the laser pulse sequence required to reach a certain final temperature may be determined. For example, the duration may be determined such that the final temperature (increase) is close to but does not exceed a certain (pain) threshold such as to avoid overly damaging the tissue and/or pain experienced by the patient, but at the same time high enough to maximize the effect of the pulse sequence. Hence, the effect of the pulse sequence may be optimized and treatment time may be minimized, but at the same time the patient's well-being is not at risk.

For example, the means for setting as described herein may comprise a user interface, in particular a graphical user interface, such as a screen or touch-screen, and/or a switch, and/or a button, and/or a scroll-bar, and/or any other functional unit that would allow the user to set a duration of the laser pulse sequence and/or a cumulative fluence of the laser pulse sequence.

For example, the means for determining may comprise a (pre-calibrated) control unit that, based on a cumulative fluence, automatically determines the duration. The duration (and/or cumulative fluence and/or final temperature (increase)) may then be displayed by the apparatus for confirmation by the operator of the apparatus. Additionally or alternatively, the duration may be automatically set. For example, the means for determining may be adapted to determine a longer duration for a pulse sequence comprising a higher cumulative fluence for application on the same predetermined target tissue.

According to a further aspect, an apparatus may be provided for generating a laser pulse sequence for application to a predetermined target tissue. The apparatus may comprise means for setting a duration t of the laser pulse sequence. Also, it may comprise means for determining a cumulative fluence $F_s$ of the laser pulse sequence as function of the duration such that the predetermined target tissue is heated to a final temperature (increase) that is within a predetermined range.

As outlined above, the inventors of the present invention have been able to establish a temperature model, linking cumulative fluence and duration of the laser pulse sequence with a final temperature (increase), on which the pain experienced by a patient depends predominantly. Hence, from a given set of cumulative fluence and pulse duration the final temperature (increase) can be determined, e.g. based on the temperature model.

Therefore, an apparatus may be provided which allows, e.g. a physician or a cosmetician, to set a predetermined duration of a laser pulse sequence to be applied (e.g. via a user interface), e.g. as defined by a maximum duration tolerable for a patient. The cumulative fluence of the laser pulse sequence required to reach a certain final temperature may be determined based thereon. For example, the cumulative fluence may be determined such that the final temperature (increase) is close to but does not exceed a certain (pain) threshold such as to avoid overly damaging the tissue and/or pain experienced by the patient but at the same time maximize the effect of the pulse sequence within the given treatment time. Hence, the effect of the pulse sequence may be optimized within the given treatment time, but at the same time the patient's well-being is not at risk.

For example, the means for determining may be adapted to determine a higher cumulative fluence for a pulse sequence comprising a longer duration for application on the same predetermined target tissue. For example, the means for determining may comprise a (pre-calibrated) control unit that, based on a duration, automatically determines the cumulative fluence. The cumulative fluence may then be displayed by the apparatus for confirmation by the operator of the apparatus. Additionally or alternatively, the cumulative fluence may be automatically set.

The apparatus may comprise a user interface via which an input may be received, e.g. from the operator of the apparatus. The input may be indicative of or be a value for the cumulative fluence $F_s$ of the laser pulse sequence. The cumulative fluence $F_s$ may then be set according to the input, e.g. by the control unit. Additionally or alternatively, the input may be indicative of or be a value for the duration $t_s$ of the laser pulse sequence. The duration $t_s$ may then be set according to the input, e.g. by the control unit. Also an input may be received which is indicative of a tissue type to which the laser pulse sequence is to be applied.

For example, for a set of values for the cumulative fluence $F_s$, corresponding suitable pre-calibrated values for the duration may be stored (e.g. specific for a tissue type). Additionally or alternatively, the control unit may be adapted to calculate values for the duration based on one or more pre-calibrated parameters and/or a pre-calibrated temperature model (e.g. specific for a tissue type).

Additionally or alternatively, for example, for a set of values for the duration $t_s$, corresponding suitable pre-calibrated values for the cumulative fluence $F_s$ may be stored (e.g. specific for a tissue type). Additionally or alternatively, the control unit may be adapted to calculate values for the cumulative fluence based on one or more pre-calibrated parameters and/or a pre-calibrated temperature model (e.g. specific for a tissue type).

The above values and/or parameters and/or the model may be stored, e.g. in a storage medium of the apparatus (or, specifically, the control unit) and/or the apparatus may comprise an interface via which they may be retrieved (e.g. from a cloud based database).

In some examples, the means for determining may be adapted to determine the duration and/or the cumulative fluence such that the final temperature (increase) is below a predetermined pain threshold temperature (increase $\Delta T_p$) specific for the predetermined target tissue. For example, the pain threshold temperature increase $\Delta T_p$ for the predetermined target tissue may be stored in a storage medium of the apparatus and/or the apparatus may comprise an interface via which it may be retrieved (e.g. from a cloud based database). The duration and/or cumulative fluence may then be determined such that the final temperature increase is below the pain threshold temperature increase $\Delta T_p$. For example, it may be selected such that the final temperature increase is within the range of 0.7 $\Delta T_p$ to 0.99 $\Delta T_p$, 0.80 $\Delta T_p$ to 0.99 $\Delta T_p$, 0.85 $\Delta T_p$ to 0.99 $\Delta T_p$, 0.85 $\Delta T_p$ to 0.95 $\Delta T_p$, 0.9 $\Delta T_p$ to 0.95 Tor approximately 0.95 $\Delta T_p$. This may allow a maximum effect of the pulse sequence but ensure that the patient does not experience any pain.

The means for determining may be adapted to determine the duration and/or cumulative fluence based on a temperature model for the final temperature (increase). The temperature model may be a function of the duration and the cumulative fluence $F_s$ of the laser pulse sequence. For a laser pulse sequence directed at the same tissue of a predetermined type (e.g. each pulse having the same flat beam or standard Gaussian spatial pulse intensity distribution), these may essentially be the only parameters included in the temperature model. In fact, the inventors of the present invention have determined, as outlined further below, in various experimental studies, that the precise number of pulses between which the cumulative fluence is distributed is not really decisive for the final temperature, as far as each individual pulse is non-ablative. The temperature model may however be specific to the type of tissue (for example, different parameters may be applied for the temperature model, e.g. as outlined herein, depending on whether the tissue type is mucosa or skin). However, this may be taken into account by receiving, by the apparatus, an input indicative of the tissue type to which the pulse sequence is to be applied.

Also the temperature model may be specific to the geometry of the laser pulse profile. For example, for a patterned (i.e., pixelated) beam comprising several spots (e.g. with each spot having a flat beam or standard Gaussian spatial pulse intensity distribution) the same pulse duration and cumulative pulse fluence may lead to a lower final temperature due to the larger cooling reservoir available for such a beam, namely in between the various spots. Also this may be taken into account by, e.g., receiving an input selecting a certain geometry of the laser pulse profile (e.g. pixelated or non-pixelated). Alternatively, this may be taken into account by the apparatus automatically detecting which handpiece (e.g. pixelated or non-pixelated) is connected to the apparatus. In other words, the apparatus may be adapted to determine whether the laser pulse sequence is to be "full beam", i.e., non-pixelated, or pixelated (e.g. based on selection input by an operator), and a pre-calibrated temperature model may be selected accordingly.

The final temperature (increase) generated by a pulse sequence as understood herein may be the temperature (increase) at time $t_s = N \times \Delta t$ after application of the first pulse of the pulse sequence, wherein N is the total number of pulses of the pulse sequence and $\Delta t$ is the average time between two subsequent pulses of the pulse sequence. More specifically, if each pulse is applied (to the tissue) at time $t_1$, $t_2, \ldots t_N$, then (N−1) times between subsequent pulses can be defined as follows $\Delta t_1 = t_2 - t_1$, $\Delta t_2 = t_3 - t_2, \ldots \Delta t_{N-1} = t_N - t_{N-1}$. Then the average time $\Delta t$ between two subsequent pulses is $\Delta t = (\Delta t_1 + \Delta t_2 + \ldots \Delta t_{N-1})/(N-1)$. Time is can also be rewritten as $t_s = N \times \Delta t = (N-1)\Delta t + \Delta t = t_N - t_1 + \Delta t$. In other words, the duration $t_s$ defined as the time between application of first and last pulses plus an additional average time between two subsequent pulses. This definition makes sure that the final temperature relates to a point in time in which transients (heat spikes that decay quickly) have relaxed and the correct long term base-line temperature is taken into account instead.

The pulse sequences of the present disclosure may generally consist of a plurality of pulses, each pulse having a duration of less than 5 ms (e.g. 3 ms or less, or 1.5 ms or less, or 1 ms or less, or 0.8 ms or less) and a wavelength which is highly absorbed in tissue and/or water, e.g. having an absorption depth of less than 100 μm. The time between two subsequent pulses may generally be in the range of 20 ms to 5000 ms, and an average temporal spacing between the pulses of a pulse sequence may be in the range of 20 ms 101000 ms.

In some examples, the laser pulses are non-ablative, i.e. they are adapted such that they do not lead to ablation of the predetermined target tissue. In some examples, each pulse or at least some of the pulses of the pulse sequence are adapted to comprise a pulse duration that is sufficiently short, such that the critical temperature of the predetermined tissue, as described herein, is above 50° C., above 70° C., above 120° C., above 180° C. or even above 250° C.

The laser pulse sequence may have a predetermined number N of pulses, and the means for determining may be adapted to determine the duration and/or the cumulative fluence such that the final temperature at time is =N×Δt after application of the first pulse of the pulse sequence is within the predetermined range, wherein Δt represents an average separation time between subsequent pulses of the pulse sequence.

In other words, based on the cumulative fluence, a time $t_s$ may be determined (or vice versa, cf. below) by the means for determining. Then, a number of pulses or an average pulse separation may be selected by the user or the apparatus which then fixes the respective other quantity (via $t_s$=N×Δt), e.g. as described herein. The apparatus may be adapted such that the pulses have individual pulse fluences that add up to the cumulative fluence, wherein the individual pulse fluence is approximately constant. When selecting N (or it), care may be taken that each individual pulse fluence remains below the ablation threshold, as further outlined herein.

For example, N can be selected as the minimum number of pulses (e.g. of approximately equal individual pulse fluence) which is needed to provide the cumulative fluence, under the condition that no individual pulse fluence is above ablation threshold and/or no individual pulse leads to a peak temperature above the critical temperature. The number of pulses can additionally be selected based on the considerations set forth herein.

The apparatus may further comprise means for setting at least one parameter indicative of the predetermined target tissue. The means for determining may be adapted to determine the duration and/or cumulative fluence based on the at least one parameter. For example, the parameter may include a tissue type (mucosa or skin, for example; whether or not the tissue is anesthetized, e.g. with topical anesthesia etc.). For example, a final temperature may be calculated based on a temperature model that is a function of the duration $t_s$, the cumulative fluence $F_s$ and the at least one parameter.

The apparatus may comprise a user interface for receiving a user input indicative of or being the at least one parameter. For example, the user may directly or indirectly specify, via the user input, the tissue type. The user interface may comprise means for allowing a selection between different tissue types. For example, the user interface may, e.g. via a graphical user interface, display (or otherwise) indicate available tissue type options to the user (such as skin or mucosa), from which the user may then select.

Additionally or alternatively, the temperature model may be a (binary) function of the pixelization of the laser pulse sequence. For example, a different scale factor may be applied in the temperature model if the laser pulse sequence is pixelated (e.g. leading to lower final temperatures).

The apparatus may further comprise means for generating the laser pulse sequence with the determined duration and/or with the determined cumulative fluence. In some examples, the means for generating the laser pulse sequence may (automatically) generate the laser pulse sequence based on the determined duration and/or the determined cumulative fluence. For example, the number of pulses may be selected (e.g. automatically, as described herein and/or upon a user selection). The laser pulse sequence may then be generated (automatically) with pulses based on the selected number N of pulses, the (determined) duration of the pulse sequence, and the (determined) cumulative fluence (e.g. the cumulative fluence may be distributed approximately equally over the number of pulses N).

Additionally or alternatively, the apparatus may comprise means for receiving a setting of the duration of the laser pulse sequence and/or a setting of the cumulative fluence of the laser pulse sequence. The apparatus may further comprise means for issuing a warning if the setting of the duration and/or the cumulative fluence deviates from the determined duration and/or the determined cumulative fluence by a predetermined threshold.

For example, the user may input a setting, e.g. via one or more user interfaces, of the pulse duration and/or the cumulative fluence. This setting may override the determined duration and/or the determined cumulative fluence. However, if the determined duration and/or cumulative fluence deviates by more than a predetermined threshold from the respective setting, a warning may be issued.

Additionally or alternatively to the aspects described herein, an apparatus for generating a laser pulse sequence for application to a predetermined target tissue may comprise: Means for setting a cumulative fluence $F_s$ of the laser pulse sequence and means for setting a duration of the laser pulse sequence is (e.g. via a user interface). The apparatus may be adapted to determine, as a function of the cumulative fluence $F_s$ and the duration of the laser pulse sequence $t_s$, a final temperature (increase) to which the target tissue would be heated after application of the laser pulse sequence. Hence, it may be put into the user's hands to select the parameters "cumulative fluence" and "pulse duration". The system may then calculate the expected final temperature (increase), as described herein. The system may be adapted to verify whether the final temperature (increase) is below a predetermined threshold, e.g. a pain threshold. If this is verified, the apparatus may be adapted to generate the laser pulses. If this is not verified, the apparatus may abort and/or issue an acoustic, and/or visual warning to the user. Additionally or alternatively, the apparatus may determine a duration and/or cumulative fluence as described herein and suggest the determined value to the user of the apparatus and/or simply override the settings accordingly.

Any of the apparatus described herein may further comprise one or more user interfaces for receiving at least one of the following: a selection input representative of the duration $t_s$ (e.g. is =N×Δt), a selection input representative of the cumulative fluence $F_s$ of the laser pulse sequence, a selection input representative of a tissue type to which the laser pulse sequence is to be applied, a selection input representative of a pixelization of the laser pulse sequence, and/or a selection input representative of a pulse separation time Δt (or a pulse number N).

For example, the selection input may include the duration, cumulative fluence, tissue type, Δt, pixelization. For example, the selection input representative of the tissue type may indicate mucosa or skin. Additionally or alternatively, it may indicate whether it is to be applied to tissue treated with topical anesthesia. In the latter case, for example a higher pain threshold temperature may be used such that a higher final temperature can be allowed by the apparatus which may lead to a higher cumulative fluence (for a given duration) and/or a shorter duration (for a given cumulative fluence).

The means for determining (e.g. control unit) may be adapted such that the final temperature increase ΔT on the target tissue caused by the application of the laser pulse sequence does not exceed a predetermined threshold. The inventors have determined that a pain threshold temperature increase $\Delta T_p$ for skin without anesthesia is about 12.7+−2° C., whereas with application of topical anesthesia, it can be increased to 16.1+−2° C., as outlined in detail herein. For mucosa, the pain threshold temperature increase $\Delta T_p$ with anesthesia is considerably higher, namely about 30° C. Therefore, the means for determining may be adapted to (automatically) determine the duration is and/or the cumulative fluence $F_s$ of the pulse sequence such that the final temperature ΔT increase on the target tissue caused by the application of the laser pulse sequence does not exceed a predetermined threshold, which depends on the tissue type. For example, for skin (no anesthesia), it may be ensured to not exceed 12.7° C. or 80% or 85% or 90% or 95% of this value. Similarly, for skin (anesthesia), it may not exceed 16.1° C. or 80% or 85% or 90% or 95% of this value. Similarly, for mucosa (anesthesia), it may not exceed 33° C. or 80% or 85% or 90% or 95% of this value. For mucosa (no anesthesia) it may not exceed 25° C. or 80% or 85% or 90% or 95% of this value. In each case, the means for determining may be adapted such that the final temperature increase is at least 75% or 80% or 85% of the respective pain temperature increase.

The above functionality may be implemented based on the insight of the present invention that the final temperature may be described by a temperature model that depends on the duration and the cumulative fluence of the laser pulse sequence.

An apparatus as described herein may generally comprise means for generating the pulse sequence, e.g. a laser source for generating the laser pulse sequence. The means for generating may be adapted to generate each pulse with a fluence below that required for ablating the predetermined tissue.

The means for determining (e.g. control unit) may be adapted to determine the duration $t_s$ and/or the cumulative fluence $F_s$ of the pulse sequence such that $(1-x_1) \Delta T_p/(A_s \times t_s^{-K_s}) < F_s < (1+x_2) \ast \Delta T_p/(A_s \times t_s^{-K_s})$, wherein $\Delta T_p$ is the pain threshold temperature increase (e.g. 22° C.), $x_1$ and $x_2$ (are margin values; e.g., $x_1=0.5$, $x_2=0.5$); wherein $K_s$ and $A_s$ are predetermined parameters, depending on the tissue type and/or the laser source.

The above range $(1-x_1)\Delta T_p/(A_s \times t_s^{-K_s}) < F_s < (1+x_2)\ast \Delta T_p/(A_s \times t_s^{-K_s})$ is based on the insight, that the final temperature increase ΔT, created on target tissue by application of a laser pulse sequence is approximately proportional to the cumulative fluence $F_s$, and can, more specifically be described by $\Delta T_s = A_s \times F_s \times t_s^{-K_s}$. This temperature increase is to be below a pain threshold temperature increase $\Delta T_p$, i.e. such that $\Delta T_s = A_s \times F_s \times t_s^{-K_s} < \Delta T_p$.

The right inequality $(F_s < (1+x_2) \ast \Delta T_p/(A_s \times t_s^{-K_s}))$ takes into account a margin $x_2$. In some examples, $\Delta T_p$ may be used as indicated above for specific tissue types (e.g. 12.7° C. for skin (no anesthesia), etc.). $x_2$ may then be selected to be zero in the above formulas, or even to be negative to allow for a safety margin, e.g. −0.05, −0.1, or −0.15, or −0.2 (which corresponds to a limit of 80% or 85% or 90% or 95% of the respective specific threshold temperature increase).

The left inequality $((1-x_1)\Delta T_p/(A_s \times t_s^{-K_s}) < F_s)$ is to ensure that the effect of the laser pulse sequence has a certain minimum effect. The final temperature increase shall be at least $(1-x_1)\Delta T_p$. Also here, a uniform threshold may be used regardless of the tissue type using a margin value $x_1$. However, also a value specific for the tissue type (e.g. as outlined above) may be used. In some examples, $x_1$ may be 0.5, 0.4, 0.3, 0.2, or 0.1, 0.05, or even 0 (to provide at least 50%, 60%, 70%, 80%, 90%, 95% or 100% of the threshold temperature increase).

For example, an apparatus may comprise an Er:YAG laser source for generating the laser pulse sequence. The means for determining (e.g. control unit) may then be adapted as outlined above wherein Ks is within the range 0.3 to 0.5, 0.35 to 0.45, or approximately 0.4. As may then be a predetermined parameter, wherein the means for determining may use and/or store (in a permanent memory) a value for this parameter depending on the tissue type and/or depending on whether the beam of the laser pulse sequence is to be pixelated.

For example, for an Er:YAG laser source, the means for determining may be adapted to determine the duration $t_s$ (in units of ms) and/or the cumulative fluence $F_s$ (in J/cm²) of the pulse sequence such that $$(1-x_1)\Delta T_p/(A_s \times t_s^{-K_s}) < F_s < (1+x_2) \ast \Delta T_p/(A_s \times t_s^{-K_s}), \qquad (0)$$

wherein $\Delta T_p$ is 22° C., $x_{1=0.5}$, $x_{2=0.5}$; wherein $K_s$=0.43 and:
$A_s$=84 (° C. cm²)/J, if human skin is the tissue type and no pixelization of the laser pulse sequence is to be used (e.g. as indicated by corresponding selection input); and/or $A_s$=69 (° C. cm²)/J, if human mucosa is the tissue type and no pixelization of the laser pulse sequence is to be used (e.g. as indicated by corresponding selection input); and/or $A_s$=28 (° C. cm²)/J, if human skin is the tissue type and pixelization of the laser pulse sequence is to be used (e.g. as indicated by corresponding selection input); and/or $A_s$=18 (° C. cm²)/J, if human mucosa is the tissue type and pixelization of the laser pulse sequence is to be used (e.g. as indicated by corresponding selection input).

The above values for $A_s$ are exemplary only, and in other examples, different values may be used, e.g. with $A_s$ selected from the range 80 to 90 or 82 to 86, instead of 84. Also, $A_s$ may be selected from the range 50 to 60 or 53 to 57, instead of 55. Also $A_s$ may be selected from the range 24 to 34, or 26 to 30, instead of 28. Finally, $A_s$ may also be selected from the range 14 to 24, or 16 to 20, instead of 18.

In some examples, the means for determining may be adapted to determine the duration $t_s$ and/or the cumulative fluence $F_s$ of the pulse sequence such that $(1-x_1) \Delta T_p/(A_s \times t_s^{K_s}) < F_s < (1+x_2)\ast \Delta T_p/(A_s \times t_s^{-K_s})$, wherein $x_1$=0.4, 0.3, 0.2, 0.1. or 0.05. In some examples, the means for determining may be adapted to determine the duration $t_s$ and/or the cumulative fluence $F_s$ of the pulse sequence such that $(1-x_1)\Delta T_p/(A_s \times t_s^{-K_s}) < F_s < (1+x_2) \ast \Delta T_p/(A_s \times t_s^{-K_s})$, wherein $x_2$=0.4, 0.3, 0.2, 0.1, 0.05, 0, −0.05, or −0.1. In other words, the apparatus may be adapted to ensure that the final temperature increase is close to but stays below the pain threshold temperature increase $\Delta T_p$. In other examples, $x_1$ and/or $x_2$ may be selected from the range 0 to 0.5, 0 to 0.3 and/or 0.1 to 0.3.

Additionally or alternatively, for the right inequality $(F_s < (1+x_2)\ast \Delta T_p/(A_s \times t_s^{-K_s}))$, $\Delta T_p$ may be used as indicated above for specific tissue types (e.g. 12.7° C. for skin (no anesthesia), etc.). $x_2$ may then be selected to be zero, or even to be negative to allow for a safety margin, e.g. −0.05, −0.1, or −0.15, or −0.2. Also in the left inequality, $\Delta T_p$ may be used as indicated above for specific tissue types, wherein $x_1$ may be 0.5, 0.4, 0.3, 0.2, or 0.1, 0.05, or even 0.

Another aspect of the present invention, which can be used independently from the further aspects described herein, but also in combination with them is an apparatus for generating a laser pulse sequence for application to a predetermined target tissue, the laser pulse sequence comprising N pulses, each laser pulse having a pulse fluence $F_i$. The apparatus may be adapted to comprise at least two predetermined modes for generating the laser pulse sequence between which can be switched. The apparatus may further comprise means for generating the laser pulses of the laser pulse sequence with an average pulse fluence $F_{ave}=(F_1+ \ldots +F_N)/N$ of the pulse sequence (and/or an average single pulse duration of the pulse sequence), such that a mean value of maximum temperature increases of the predetermined target tissue caused by each of the individual pulses of the pulse sequence is within one of the following three ranges in the first mode and within a disparate one of the following three ranges in the second mode: 5° C. to 30° C.; 30° C. to 65° C.; 65° C. to 135° C. The apparatus may further comprise means for determining $F_{ave}$ (e.g. a precalibrated control unit) which may be associated with the means for generating.

The above temperature ranges are based on the insight of the inventors that a treatment with strong temperature peaks caused by individual pulses (e.g. 65° C. to 135° C.) will lead to a strong superficial triggering effect which is desirable for various applications. For other applications it is preferable to obtain a deep coagulation effect which can be favored by using smaller temperature peaks of individual pulses (e.g. 5° C. to 30° C.). In particular, using such small spikes, more pulses can be applied until the pain threshold temperature increase is reached. With intermediate peaks (e.g. 30° C. to 65° C.) a mix of both effects may be obtained.

The means for generating the laser pulse sequence may comprise a laser source. The above functionality may be implemented by a control unit associated with the laser source, e.g. the control unit as described herein.

The apparatus may comprise a user interface for receiving a selection input based on which the means for generating and/or the control unit sets the first mode or the second mode.

The user interface may be adapted such that the selection input includes a first selection input representative of a tissue type, and the means for generating and/or the control unit (automatically) sets the average pulse fluence depending on the first selection input.

Similarly as described herein for the final temperature, the maximum temperature increase caused by a single pulse of the laser pulse sequence can be modeled, as found out by the inventors of the present invention, as a function of the pulse duration and the pulse fluence. Accordingly, the means for generating and/or the control unit may be adapted to set the average pulse fluence based on a temperature model for the maximum temperature increase, wherein the temperature model is a function of a predetermined average pulse duration of the N pulses of the pulse sequence and the average pulse fluence $F_{ave}$.

The average pulse duration and/or the average fluence may e.g. be selected via a user interface of the apparatus, e.g. as described with reference to the pulse sequence duration and/or the cumulative fluence. The respective other quantity may then be determined by the apparatus. The selected/determined quantities may then be automatically set and/or presented to the user for confirmation, e.g. as outlined above for pulse sequence duration and cumulative fluence. Also, the (average) pulse duration and/or the (average) pulse fluence and/or the corresponding maximum temperature increase may be displayed to the user.

For example, the apparatus may comprise an Er:YAG laser source for generating the laser pulse sequence which may be adapted to be applied on human skin or human mucosa. The means for generating and/or the control unit may be adapted to set the average pulse fluence $F_{ave}$ (in units of J/cm²) and/or the duration $t_p$ (in units of milliseconds) such that to $65/(A_p \times t_p^{-K_p}) < F_{ave} < 135/(A_p \times t_p^{-K_p})$ to obtain the average temperature increase of the target tissue caused by each pulse of the pulse sequence to be within the range of 65° C. to 135° C.; and/or $30/(A_p \times t_p^{-K_p}) < F_{ave} < 65/(A_p \times t_p^{-K_p})$ to obtain the average temperature increase of the target tissue caused by each pulse of the pulse sequence to be within the range of 30° C. to 65° C.; and/or $5/(A^p \times t_p^{-K_p}) < F_{ave} < 30/(A_p \times t_p^{-K_p})$ to obtain the average temperature increase of the target tissue caused by each pulse of the pulse sequence to be within the range of 5° C. to 30° C.;

wherein $t_p$ is an average pulse duration of the N pulses of the pulse sequence in units of milliseconds, and wherein $K_p=\frac{1}{3}$, and wherein the full-beam values are $A_p=173$ for skin and are $A_p=144$ for mucosa. The corresponding values for the patterned beam are $A_p=81$ for skin, and $A_p=67$ for mucosa. In some examples, each pulse may comprise approximately the same pulse duration and/or approximately the same pulse fluence.

For example, together with the pulse duration and cumulative fluence values, as determined herein, the number of pulses and their temporal spacing is also well-defined.

For example, the apparatus may comprise one or more user interfaces via which it may receive a selection input indicative of one of the at least two modes which may then be selected by the apparatus. Moreover, further selection input may be received which indicates human skin or human mucosa as the tissue type to be treated. The average fluence of the pulse sequence may then be set accordingly, e.g. according to the above inequalities. For example, each pulse may be set to comprise a fluence approximately equal to the average fluence. Possibly, another selection input may be received indicating a pulse sequence duration or a cumulative pulse fluence. The respective other quantity may then be determined by the apparatus, as described herein. As a result, the number of pulses and their temporal spacing is also well-defined and optimized.

Separately and independently from the aspects described herein, but possibly also in combination with them, an apparatus may be provided for generating a laser pulse sequence for application to a predetermined target tissue, e.g. for tissue regeneration (e.g. skin tightening, etc.). In some examples of skin or mucosa treatments, the pulse sequence comprises between 6 and 40 pulses, preferably between 10 and 40, most preferably between 12 and 30. The apparatus may be adapted to apply the pulse sequence in a non-pixelated manner, and the cumulative fluence $F_s=F_1+ \ldots +F_N$ of the pulse sequence may be i) for mucosa between 1.5 and 8 J/cm², preferably between 2.0 and 6 J/cm², most preferably between 2.5 and 5 J/cm²; and ii) for skin between 1.0 and 6.5 J/cm², preferably between 1.5 and 5 J/cm², most preferably between 1.5 and 4 J/cm². The apparatus may also be adapted to apply the pulse sequence in a pixelated manner, and the cumulative fluence $F_s=F_1+ \ldots +F_N$ of the pulse sequence may be i) for mucosa between 4.5 and 24 J/cm², preferably between 6.5 and 18 J/cm², most preferably between 6.5 and 15 J/cm²; and ii) for skin between 3.5 and 20 J/cm², preferably between 4.5 and 15 J/cm², most preferably between 4.5 and 10 J/cm². This implementation allows a particularly beneficial focus on superficial triggering without exceeding the pain threshold. The sequence duration may be set such that the final temperature is close to or just below the pain threshold, as described herein, e.g. according to equation (o). For example, sequence durations of about t=0.3–10 s may be used. The single pulse duration may optionally be selected suitably, e.g. to be 1 ms or below, e.g. 0.5 ms or below or about 0.3 ms. The above parameter (combination) may be stored on the apparatus (e.g. a storage medium, e.g. associated with a control unit), such that the parameter combination may be automatically set, e.g. in the form of a mode that may be selected, e.g. a mode for favoring superficial triggering. Hence, the apparatus may be specifically provided with a mode for superficial triggering.

Also, separately and independently from the aspects described herein, but possibly also in combination with them, an apparatus may be provided for generating a laser pulse sequence for application to a predetermined target tissue, e.g. for tissue regeneration (e.g. skin tightening, etc.). In some examples, the pulse sequence comprises between 60 and 300 pulses, preferably between 80 and 200, most preferably between 80 and 130 or 90 and 130. The apparatus may be adapted to apply the pulse sequence in a non-pixelated manner, and the cumulative fluence $F_s = F_1 + \ldots + F_N$ of the pulse sequence may be between 3 and 30 J/cm² (e.g. 3 to 20 J/cm² for skin, 5 to J/cm² for mucosa), preferably between 7 and 18 J/cm² (e.g. 7 to 15 J/cm² for skin, 9 to 18 J/cm² for mucosa), most preferably between 10 and 16 J/cm² (e.g. 10 to 15 J/cm² for skin, 12 to 16 J/cm² for mucosa). The apparatus may also be adapted to apply the pulse sequence in a pixelated manner, and the cumulative fluence $F_s = F_1 + \ldots + F_N$ of the pulse sequence may be about three times the values indicated in the preceding sentence. The sequence duration may be set such that the final temperature is close to or just below the pain threshold, as described herein, e.g. according to equation (o). For example, sequence durations of about t=5-30 s may be used. The single pulse duration may optionally be selected suitably, e.g. to be 1 ms or below, e.g. 0.5 ms or below or about 0.3 ms. The above parameter (combination) may be stored on the apparatus (e.g. a storage medium, e.g. associated with a control unit), such that the parameter combination may be automatically set, e.g. in the form of a mode that may be selected, e.g. a mode for favoring deep coagulation. Hence, the apparatus may be specifically provided with a mode for deep coagulation.

Further, separately and independently from the aspects described herein, but possibly also in combination with them, an apparatus may be provided for generating a laser pulse sequence for application to a predetermined target tissue, e.g. for tissue regeneration (e.g. skin tightening, etc.). In some examples, the pulse sequence comprises 40 to 90 pulses, e.g., 50 to 80 pulses. The apparatus may be adapted to apply the pulse sequence in a non-pixelated manner, and the cumulative fluence $F_s = F_1 + \ldots + F_N$ of the pulse sequence may be between 5 and 15 J/cm² (e.g. between 7 and 12 J/cm²), particularly between 5 and 10 J/cm² for skin and 10 and 15 J/cm² for mucosa. The apparatus may also be adapted to apply the pulse sequence in a pixelated manner, and the cumulative fluence $F_s = F_1 + \ldots + F_N$ of the pulse sequence may be about three times the values indicated in the preceding sentence. The sequence duration may be set such that the final temperature is close to or just below the pain threshold, as described herein, e.g. according to equation (o). For example, sequence durations of about T=0.6-12 s may be used. The single pulse duration may optionally be selected suitably, e.g. to be 1 ms or below, e.g. 0.5 ms or below or about 0.3 ms. The above parameter (combination) may be stored on the apparatus (e.g. a storage medium, e.g. associated with a control unit), such that the parameter combination may be automatically set, e.g. in the form of a mode that may be selected, e.g. a mode for favoring a combination of superficial triggering and deep coagulation. Hence, the apparatus may be specifically provided with a mode for a combination of superficial triggering and deep coagulation.

According to a further aspect, a method is provided for generating a laser pulse sequence for application to a predetermined target tissue. The method may comprise setting a cumulative fluence $F_s$ of the laser pulse sequence. Further, it may comprise determining a duration of the laser pulse sequence as a function of the cumulative fluence such that the predetermined target tissue is heated to a final temperature that is within a predetermined range. The method may be provided for tissue regeneration (e.g. skin regeneration), tissue resurfacing, skin tightening, removal of wrinkles. Other applications may be hair regrowth, treating urinary incontinence, fecal incontinence, erectile dysfunction and/or snoring related sleep disorders.

According to another aspect, a method is provided for generating a laser pulse sequence for application to a predetermined target tissue. The method may comprise setting a duration $t_s$ of the laser pulse sequence. Further, the method may comprise determining a cumulative fluence $F_s$ of the laser pulse sequence as a function of the duration such that the predetermined target tissue is heated to a final temperature that is within a predetermined range. The method may be provided for tissue regeneration, tissue resurfacing, skin tightening, removal of wrinkles etc.

Another aspect of the present invention, which can be used independently from the further aspects described herein, but also in combination with them, is a method for generating a laser pulse sequence for application to a predetermined target tissue. The method may be provided for tissue regeneration, tissue resurfacing, skin tightening, removal of wrinkles etc. The laser pulse sequence may comprise a predetermined duration $t_s$ and a predetermined number of N sequential laser pulses, each laser pulse having a predetermined pulse fluence $F_i$. The method may comprise: switching to a first mode of at least two predetermined modes for generating the laser pulse sequence, and setting, in the first mode, an average pulse fluence $F_{ave} = (F_1 + \ldots + F_N)/N$ of the pulse sequence, such that a mean value of maximum temperature increases of the predetermined target tissue caused by the individual pulses of the pulse sequence is within a first one of the following three ranges: 5° C. to 30° C.; 30° C. to 65° C.; 65° C. to 135° C. The method may further comprise switching to a second mode of the at least two predetermined modes for generating the laser pulse sequence, and setting, in the second mode, an average pulse fluence $F_{ave} = (F_1 + \ldots + F_N)/N$ of the pulse sequence, such that a mean value of maximum temperature increases of the predetermined target tissue caused by the individual pulses of the pulse sequence is within a disparate second one of the following three ranges: 5° C. to 30° C.; 30° C. to 65° C.; 65° C. to 135° C.

A further aspect relates to a method for superficial triggering of a predetermined target tissue for tissue regeneration and/or skin tightening and/or wrinkle removal by applying a laser pulse sequence to the predetermined target tissue. The laser pulse sequence may comprise a number of N sequential laser pulses, each laser pulse having a pulse fluence $F_i$. The method may further comprise setting an average pulse fluence $F_{ave}=(F_1+ \ldots +F_N)/N$ of the pulse sequence, such that a mean value of maximum temperature increases of the predetermined target tissue caused by the individual pulses of the pulse sequence is within 65° C. to 135° C.

According to another aspect, a method is provided for combining superficial triggering and deep coagulation of a predetermined target tissue for tissue regeneration and/or skin tightening and/or wrinkle removal by applying a laser pulse sequence to the predetermined target tissue. The laser pulse sequence may comprise a number of N sequential laser pulses, each laser pulse having a pulse fluence $F_i$. The method may comprise: setting an average pulse fluence $F_{ave}=(F_1+ \ldots +F_N)/N$ of the pulse sequence, such that a mean value of maximum temperature increases of the predetermined target tissue caused by the individual pulses of the pulse sequence is within 30° C. to 65° C.

A further aspect relates to a method for deep coagulation of a predetermined target tissue for tissue regeneration for tissue regeneration and/or skin tightening and/or wrinkle removal by applying a laser pulse sequence to the predetermined target tissue.

The laser pulse sequence may comprise a number of N sequential laser pulses, each laser pulse having a pulse fluence $F_i$. The method may comprise: setting an average pulse fluence $F_{ave}=(F_1+ \ldots +F_N)/N$ of the pulse sequence, such that a mean value of maximum temperature increases of the predetermined target tissue caused by the individual pulses of the pulse sequence is within 5° C. to 30° C.

According to a further aspect, an apparatus may be provided for generating a laser pulse sequence for application to a predetermined target tissue. The laser pulse sequence may comprise a number of N sequential laser pulses, each laser pulse having a pulse fluence $F_i$. The apparatus may comprise means for generating the laser pulse sequence with an average pulse fluence $F_{ave}=(F_1+ \ldots +F_N)/N$ of the pulse sequence, such that a mean value of maximum temperature increases of the predetermined target tissue caused by the individual pulses of the pulse sequence is within 5° C. to 30° C. The apparatus may specifically be adapted for favoring deep coagulation. The means for generating may be associated with a pre-calibrated control unit adapted to set the pulse fluence accordingly, e.g. upon a selection of deep coagulation mode and/or a skin type and/or a beam geometry by the user, as described herein.

According to a further aspect, a scanner may be provided. The scanner may be adapted to provide, at one and the same position, a pulse sequence as described herein. At the same time, the scanner may switch, in between applying subsequent pulses of the pulse sequence, at least one further pulse to another position. As a result, a pulse sequence as described herein may be provided at two or more positions, such that the frequency with which the laser pulses are applied globally may be much higher than that of the pulses applied to a certain position. Hence, treatment time can be reduced, especially, when treating larger body areas, and the full laser frequency may actually be harnessed for treatment speed.

The scanner may be adapted to distribute the laser pulses delivered by a laser source, e.g. of an apparatus as described herein, over a treatment area (consisting of many single spots or positions) and to automatically calculate an optimal scanning pattern.

For example, in case the laser operates at f=30 Hz, and the treatment requires N=5 laser pulses to be delivered at a repetition rate of 6 Hz, then the scanner will decide to treat 5 spots one after another and return to the original position for the sixth pulse. The scanner will be moving from one spot to another at Hz but each spot will experience pulses at a repetition rate of only 30/5=6 Hz. Once all N=5 pulses are delivered to each spot, the scanner moves to the next group of 5 spots. Since all combinations of N and $F_p$ are not possible for any selected overall body area, the scanner may decide not to treat in this way adjacent 5 spots but may select other spatially optimally positioned sets. Of course, the above numerical examples are only exemplary and other numerical values may be implemented.

For example, an apparatus as described herein may comprise a scanner, such that a first pulse sequence as described herein is automatically applied to a first position of the target tissue and a second pulse sequence as described herein is automatically applied to a second position of the target tissue, wherein the application of the first and second pulse sequences overlaps temporally. The automatic application may be such that a first pulse of the second pulse sequence is applied at a time interval after a first pulse of the first pulse sequence, wherein the time interval may be approximately equal to the inverse of the maximum frequency $f_{max}$ at which laser pulses can be delivered by a laser pulse source of the apparatus.

In one of the embodiments, the separation time, i.e., the time between two subsequent pulses $\Delta t$ and the scanning pattern may be determined by the time interval $\Delta t_{max}$ that is equal to the inverse of the maximum laser frequency $f_{max}$. In this embodiment, the separation time can assume only values equal to $\Delta t=J \times \Delta t_{max}$, where J is an integer. The sequence time is then determined according to $t_s=N \times J \times \Delta t_{max}$. Similarly, the scanner selects the maximal total number M of laser spots that fit into the selected scan area, that satisfies the condition that the ratio K=M/J is an integer. The total area is covered by the scanner by sequentially irradiating K sets consisting of J spots, each spot within a set receiving N laser pulses separated by $\Delta t=J \times \Delta t_{max}$. The scanner may in one embodiment select sets such that at least spots within each set are adjacent to each other. In yet another embodiment, the scanner may select sets such that spots within at least one set, at least K−1 sets or all sets are not adjacent to each other, in order to reduce superficial overlapping of the delivered heat. In case they are not adjacent to each other this reduces "cross-talk" among them, e.g. due to thermal diffusion in in the radial direction.

A further aspect of the present disclosure is a computer program which may include instructions for carrying out the steps of the methods and/or implementing the functionalities outlined herein, when the instructions are executed by a processor. In some examples, the claimed apparatus may comprise a storage medium storing such program, and a processor or microcontroller configured to execute the program, causing the respective means of the apparatus to implement the functionality as described herein. For example a control unit comprising such processor or microcontroller may be provided.

It is noted that the methods as described herein may comprise one or more additional method steps which correspond to any of the functionalities as described herein, even if the functionality is only described with respect to an apparatus or otherwise. In turn, each functionality described herein with respect to a method may be implemented in an apparatus having means and/or a computer program having

4. BRIEF DESCRIPTION OF THE FIGURES

Figure 1B:
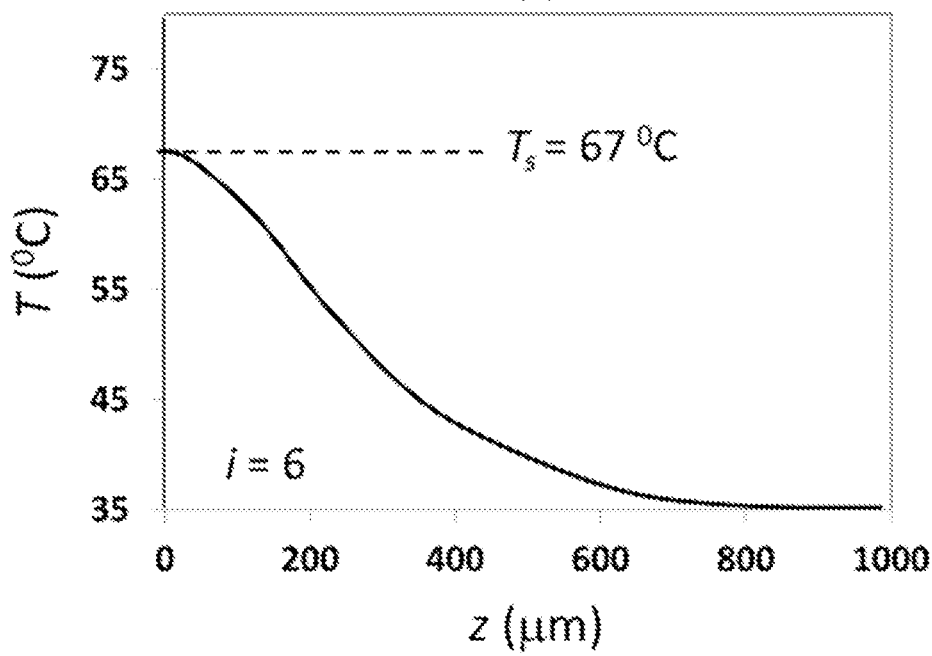
Figure 2:
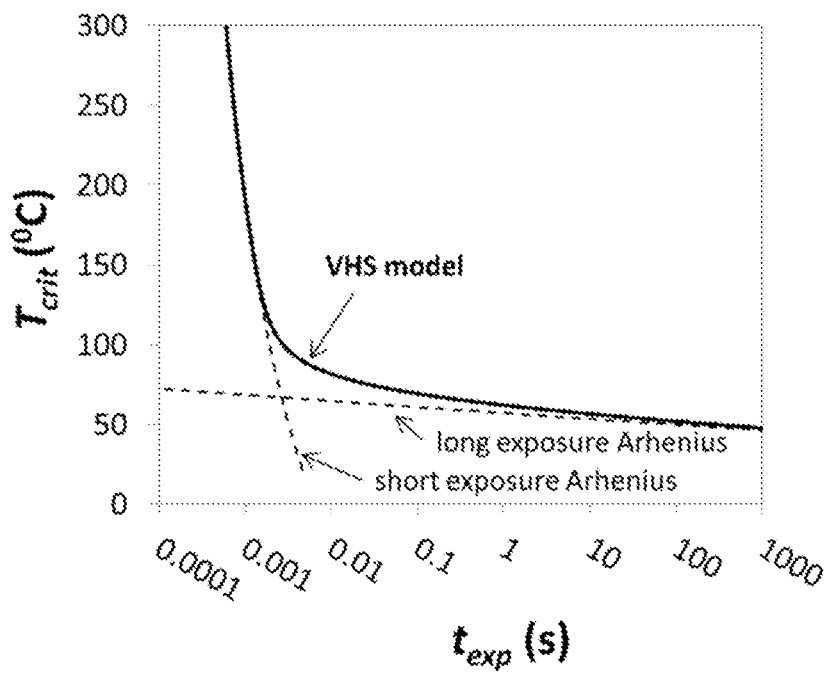

FIGS. 1A, 1B: Exemplary temporal and spatial temperature profiles during and following a laser pulse sequence (with N=6 and $t_{sep}$=50 ms);

FIG. 2: Shows the critical temperature as a function of the exposure time, the function representing a combined effect of two limiting Arrhenius' processes, defining cell viability at extremely long and short exposure times.

Figure 3:
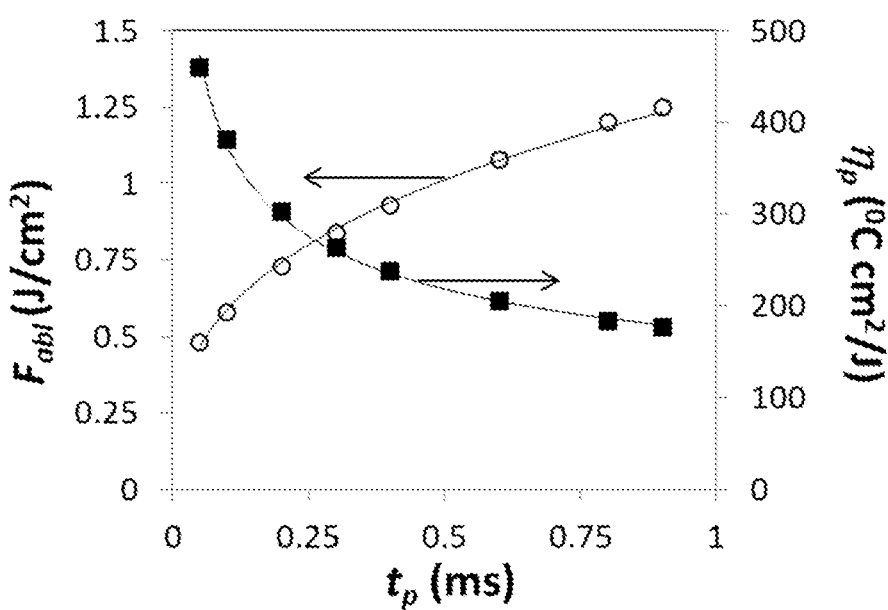
Figure 4:
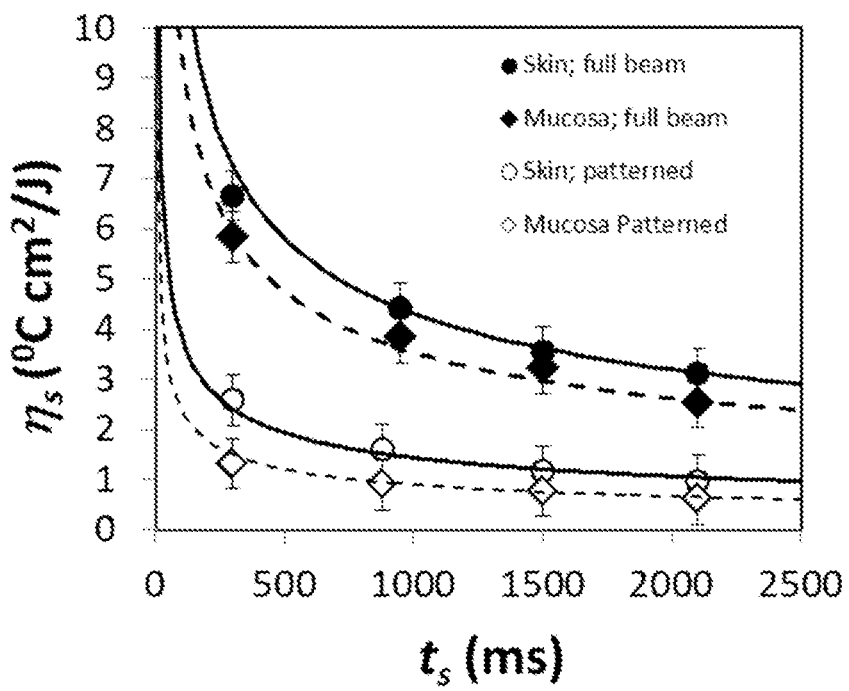
Figure 7:
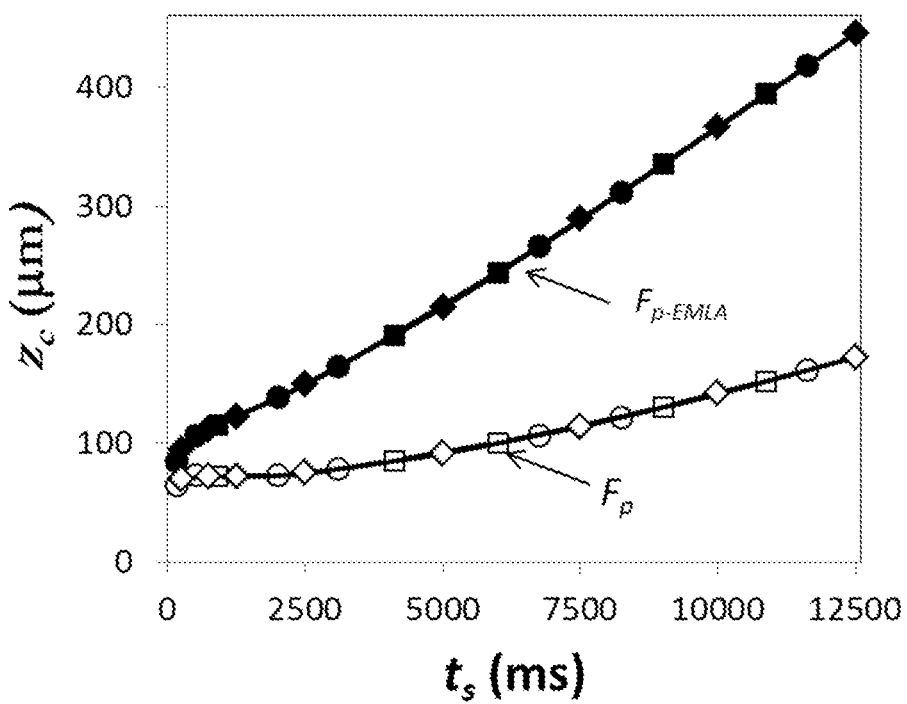
Figure 5A:
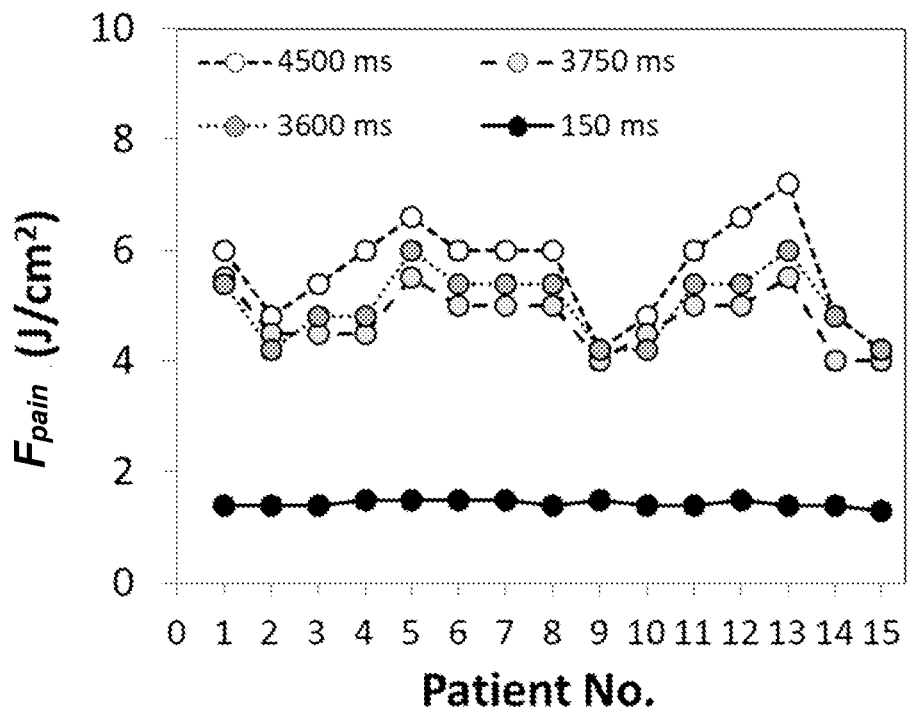
Figure 6A:
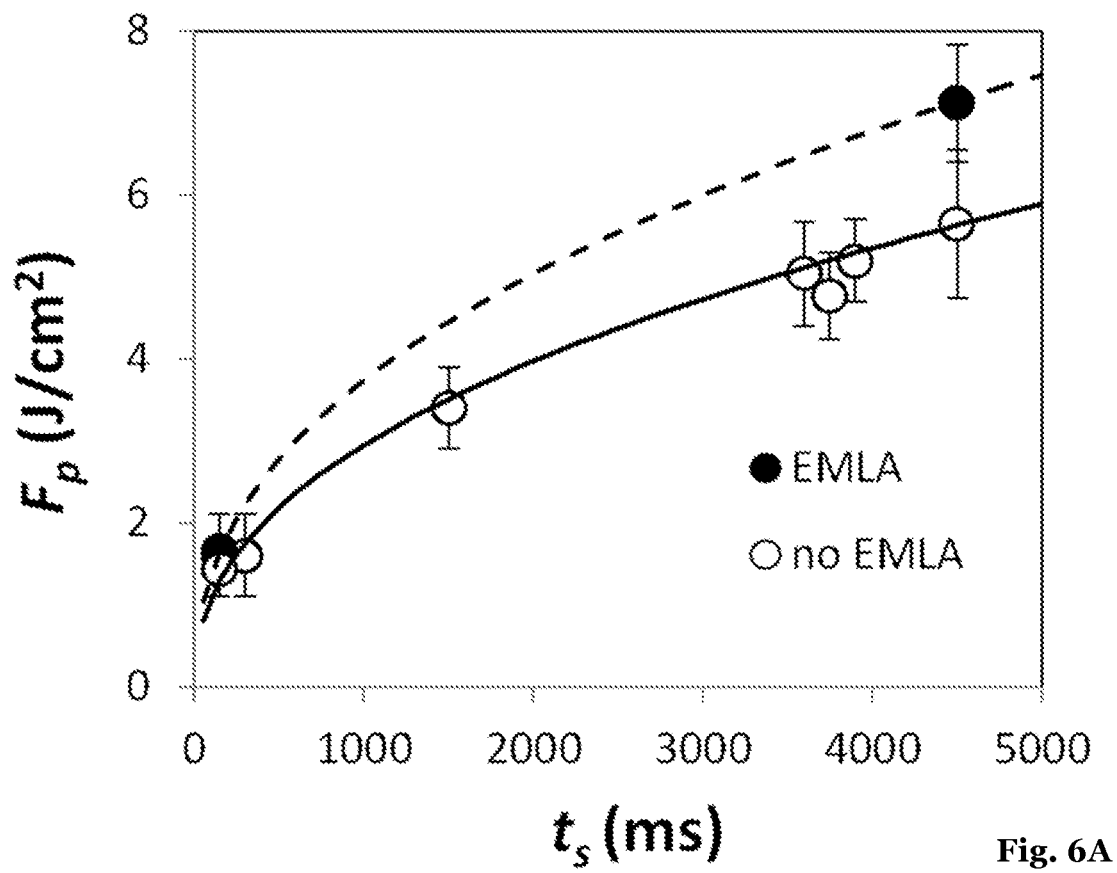
Figure 8A:
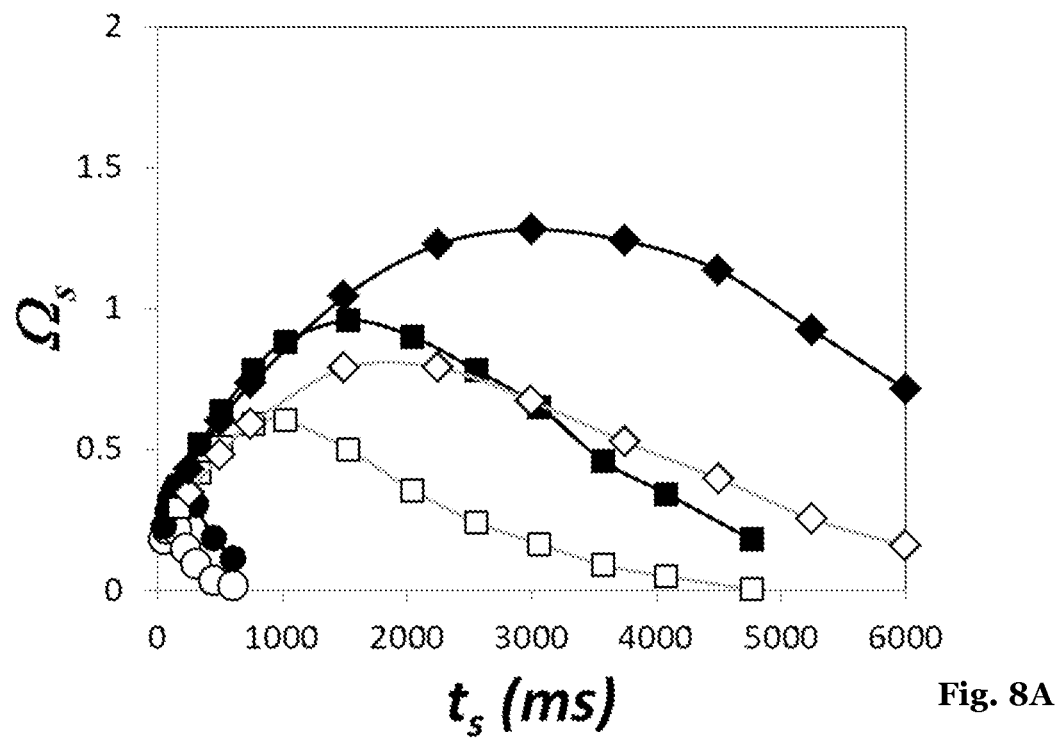
Figure 9:
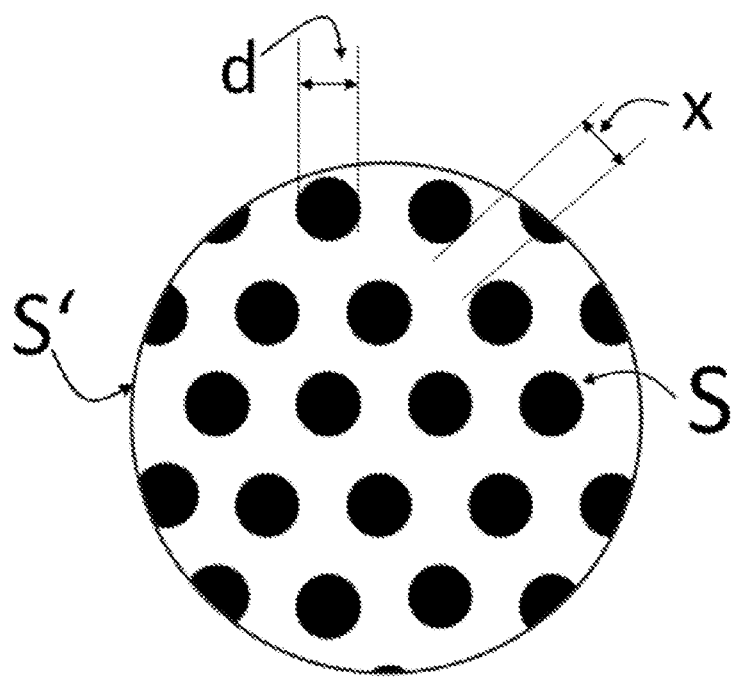
Figure 11:
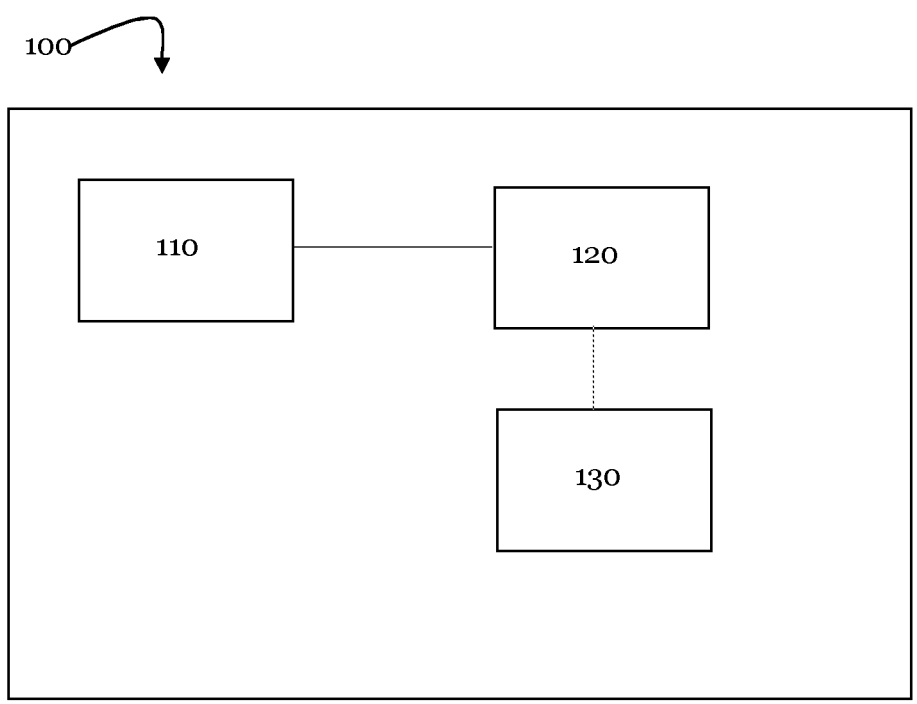
Figure 10A:
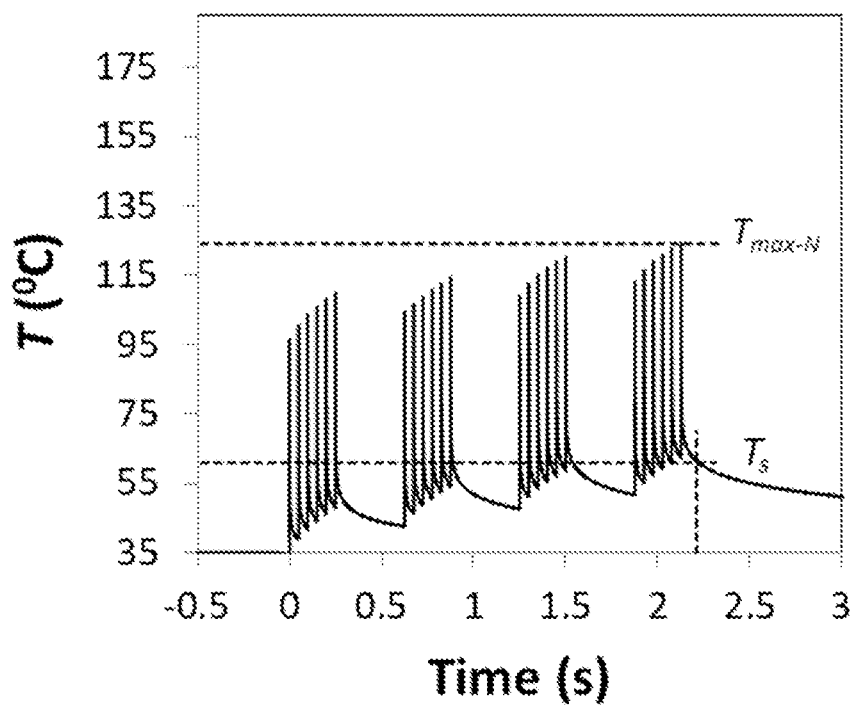
Figure 10B:
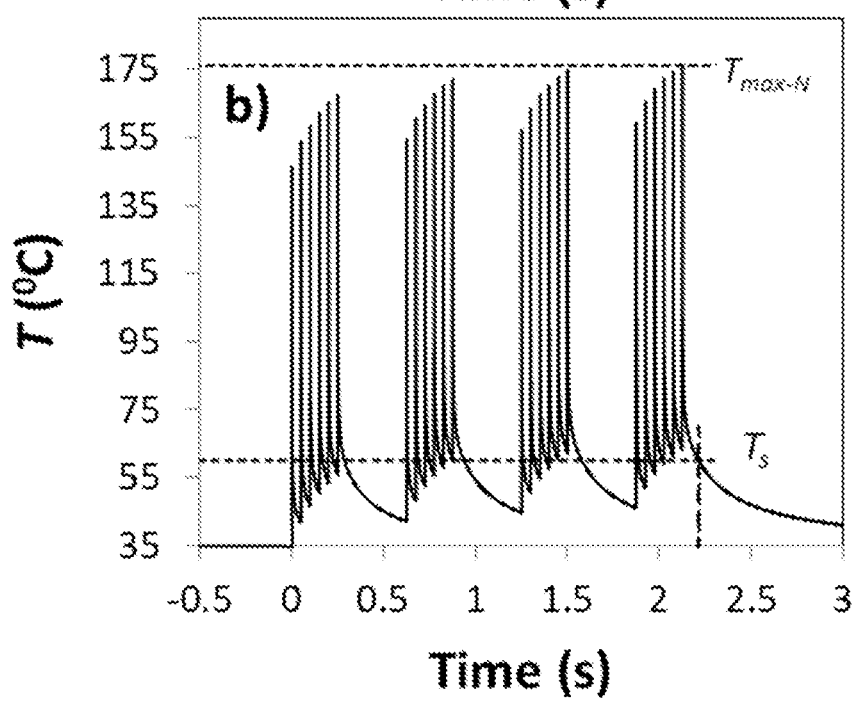

FIG. 3: Calculated dependence of the single-pulse ablation threshold fluence ($F_{abl}$) and single pulse temperature slope ($\eta_p = \Delta T_{max}/F_p$) on the Er:YAG single-pulse duration ($t_p$);

FIG. 4: Measurements and simulated dependence of the sequence temperature slope ($\eta_s = \Delta T_s/F_s$) on the sequence duration $t_s$ for full-beam and patterned beam treatment of skin and mucosa;

FIGS. 5A, B: Show cumulative pain threshold fluences $F_{pain}$(J/cm$^2$) for various pulse sequence durations and patients;

FIG. 6a,b: Show the dependence of the measured pain threshold fluence $F_{pain}$ and pain threshold temperature increase on the sequence duration $t_s$;

FIG. 7: Shows the calculated long-exposure coagulation depths $z_c$ (μm) as a function of the sequence duration $t_s$ (ms);

FIGS. 8A, B: Show the calculated short-exposure superficial damage ($\Omega_s$) as a function of the sequence duration $t_s$ (FIG. 10a) or number of pulses N (FIG. 10B);

FIG. 9: Shows the spatially patterned (i.e., pixelated) delivery of laser pulses FIGS. 10A, B: Shows the evolution of pulse peak temperatures $T_{max-i}$ for each pulse and of the heat shock triggering amplitude $A_{trig}$ after each set of 6 pulses during a heat shocking triggering;

FIG. 11: Exemplary embodiment of an apparatus according to the present invention.

5. DETAILED DESCRIPTION

Ablative skin resurfacing using $CO_2$ and Er:YAG lasers has proven to be an effective and reproducible method for treating wrinkles. Of particular interest has been resurfacing with the Er:YAG laser wavelength since it allows for the so-called "cold" ablation with minimal thermal damage below the ablation front. This unique erbium laser characteristic has been attributed to the extremely short optical penetration depth (δ) in human soft tissues of only several microns, the shortest penetration of all non-ultraviolet lasers. This is because the Er:YAG laser wavelength is positioned at the highest far-infrared water-absorption peak of λ=2940 nm. In erbium laser procedures, it is therefore the tissue's water content, not its pigment, that plays the role of an absorbing chromophore. The laser-induced temperature elevation ΔT is thus not limited to a particular pigment, such as melanin or hemoglobin, but to the superficially irradiated tissue layer with its thickness determined by the laser's extremely short optical penetration depth.

The laser-induced temperature elevation $t_s$ accompanied by the chemical process of protein denaturation as a result of the cellular exposure to the increased temperature.

The tissue damage is typically calculated using the Arrhenius damage integral Ω calculated over the time of the thermal exposure ($t_{exp}$) and the related critical temperature ($T_{crit}$), representing the temperature at which the concentration of the undamaged tissue is reduced by the Euler's number e.

According to the Arrhenius damage integral, the tissue injury grows exponentially with the elevated temperature T, and linearly with the time of exposure $t_{exp}$. During pulsed laser procedures, the duration of the heat shock, i.e. of the thermal exposure, $t_{exp} \approx t_p + t_d$, is not determined only by the duration of the laser pulse $t_p$, but typically much more by the temperature decay time td required for the irradiated tissue layer to cool back down to the initial temperature. For the superficially absorbed lasers, the temperature decay time $t_d$ depends strongly on the optical penetration depth according to $t_d \approx \delta^2/D$, where D is the tissue's thermal diffusivity [1: Majaron B, Sustercic D, Lukac M, Skaleric U, Funduk N. Heat diffusion and debris screening in Er:YAG laser ablation of hard biological tissues. Appl Phys B 1998; 66:479-487, 7; 2: Majaron B, Plestenjak P, Lukac M. Thermo-mechanical laser ablation of soft biological tissue: modeling the micro-explosions. Appl. Phys. B 1999; 69, 71-80]. Short thermal exposures can therefore be achieved only by short-pulsed lasers with strong absorption in tissues. Here, Er:YAG is at a significant advantage due to its highest absorption in tissue water, enabling thermal exposure times below one millisecond [3: Lukac M, Lozar A, Perhavec T, Bajd F. Variable heat shock response model for medical laser procedures, Lasers Med Sci. August 2019; 34(6):1147-1158]. For example, the exposure time may be approximated by $$t_{exp} \approx t_{ed} + t_d$$

The importance of td being very short can be better understood by considering that during tissue resurfacing, the superficial tissue is typically heated up to the ablation temperature $T_{abl}$ at which the tissue ablation starts as a result of micro-explosions of overheated tissue water within the elastic soft tissue. Since the water contained within the confined solid tissue cannot expand freely, the ablation temperature is not at the boiling temperature of water, under atmospheric pressure of about 100° C., but at a much higher temperature of $T_{abl} \approx °$ C. [2, 3]. According to the standard Arrhenius model of skin damage, the critical temperature would be much lower, around 55-65° C. However, for extremely short exposure times, the critical temperatures are significantly higher than what would be expected from the standard single process Arrhenius model. For thermal exposure times attainable by Er:YAG resurfacing, the critical temperature is above 250° C. This is shown in FIG. 2 which shows the critical temperature as a function of the exposure time [3] (VHS: variable heat shock).

While ablative laser resurfacing procedures have been found to be extremely effective, a major disadvantage is the erosion of large surfaces, which necessitates a recuperation period of 1 to 2 weeks. There are also potential risks of infections, scarring or hyper- and hypo-pigmentation. For this reason, it has been proposed to utilize the unique superficial absorption characteristics of Er:YAG also for less invasive non-ablative treatments. As opposed to ablative procedures, the main mechanism of action of non-ablative procedures is based on selective thermal damage followed by new collagen formation. The depth of the tissue's thermal response, i.e., of the tissue coagulation, is determined by the amount of heat that can be delivered to the tissue in a non-ablative manner. Since in the absence of thermal diffusion the ablation threshold fluence $F_{abl}$ (in J/cm$^2$), is inversely proportional to δ, the heat energy that can be delivered into the tissue by a single Er:YAG laser pulse is relatively small. This applies especially since the existing Er:YAG laser technology limits single pulse durations to below several milliseconds, limiting the time available for conductive superficial cooling of the tissue during the laser pulse. It is for this reason that non-ablative Er:YAG treatments have been performed by repetitive stacking of sub-threshold Er:YAG laser pulses, resulting in a higher cumulatively delivered sequence fluence, $F_i$.

Initial studies of non-ablative thermal treatments with repetitive stacking of Er:YAG laser pulses were made at cumulative fluences ($F_s$) close to the ablation threshold. This resulted in a significant damage to the epidermis, leading to subsequent peeling of the damaged epidermis, making the treatments "delayed ablative". Therefore, with this type of non-ablative resurfacing, the epithelium is in reality damaged, but not completely removed during the procedure, and acts as a wound dressing. For this reason, this type of sub-ablative (or minimally ablative) resurfacing modality can be called also a "sub-resurfacing" modality.

This invention describes a different resurfacing modality, further referred to also as the smooth-resurfacing modality where the applied fluences are not only below the ablation threshold but also below the patient's pain threshold. Pain threshold fluences were measured for abdominal skin with and without topical anesthesia and compared with measured superficial tissue temperature evolution during smooth-resurfacing of the skin and oral mucosa. The obtained temperature data and pain thresholds were then used to study the characteristics of the short- and long-exposure's tissue response believed to be respectively involved in the indirect and direct soft-tissue regeneration mechanisms.

With smooth-resurfacing, indirect regeneration mechanisms in addition to the direct heat injury to the deeper lying connective tissues play a role in regeneration and remodeling of the treated tissue. This indirect triggering of tissue regeneration through short-exposure intense heat shocking of epithelia is based on stimulating signal transduction processes for transcription factor activation, gene expression and fibroblast growth, leading to new collagen and extracellular matrix formation.

a) PHYSICAL MODEL OF RESURFACING

A numerical model may be applied for the physical process of sub- and smooth-resurfacing of soft tissues, such as skin and mucosa, based on that developed to study thermo-mechanical ablation with mid-IR lasers. The details of that model are described in [4: Majaron B, Plestenjak P, Lukac M. Thermo-mechanical laser ablation of soft biological tissue: modeling the micro-explosions. Appl. Phys. B 1999; 69, 71-80].

Based on the model, we assume that a single wavelength ($\lambda$) pulsed laser radiation is delivered to the surface of the treated tissue with a pulse fluence $F_p$ (in J/cm²). The tissue is modeled as a water-containing homogeneous media characterized by a single absorption coefficient of $k=1/\delta$ for the delivered laser wavelength $\lambda$. For simplicity, a square-shaped laser pulse with duration $t_p$ is assumed. If the focus is on the Er:YAG laser wavelength with a short penetration depth, effects of scattering of the laser light within the tissue can be excluded. Similarly, it may be assumed that that the laser spot size is much larger than the penetration depth $\delta$. Therefore, the diffusion of dissipated heat may be treated in one dimension using a finite-difference scheme. In all calculations, we use the physical parameters of the irradiated media as published in [2].

To elucidate at what individual pulse fluence $F_p$ and total sequence fluence $F_s$ the laser-tissue interaction starts being ablative, the model also includes the microscopic physical model of the ablative micro-explosion process, which combines the thermodynamic behavior of tissue water with the elastic response of the solid tissue components.

The model was applied to calculate temporal and spatial temperature profiles for single pulses and as well for pulse sequences, each consisting of N consecutive Er:YAG laser pulses with individual $F_p$ and cumulative $F_s$ fluences, separated by a pulse separation time $t_{sep}$. The effective duration of the modeled pulse sequences was defined by the sequence duration $t_s = N \times t_{sep}$.

FIG. 1A shows a typical temporal profile of the tissue surface temperature, T (° C.) during a pulse sequence over the course of time in seconds, t(s). It is noted that, unless indicated otherwise, the tissue temperatures as defined herein pertain to tissue surface temperatures. The pulse sequence comprises N=6 pulses at a separation time of $t_{sep}=50$ ms, and comprises a duration indicated as $t_s$, wherein $t_s=N \times t_{sep}$. The pulse sequence results in N high temperature peaks (designated by the reference sign $T_{max-i}$) that rapidly relax deeper into the tissue by fast thermal diffusion driven by the large temperature gradient over the short optical absorption length. Due to the fast thermal diffusion from the heated ≈1-3 μm thin superficial tissue layer, the duration of the thermal exposure ($t_{exp}$) to high temperature peaks $T_{max-i}$ is extremely short (it can be as short as $t_{exp}<1$ ms but can also be longer). During the pulse sequence, the superficially laser-generated heat is thus being "pumped" by diffusion away from the epithelia, up to several hundred microns deep into the connective tissue (see FIG. 1B). The final, longer persisting surface temperature is in FIG. 1A represented by the sequence temperature $T_s$ (at $t=t_s=N \times t_{sep}$).

FIG. 1B shows the resulting spatial profile of the tissue temperature, T (° C.) within the tissue depth, z (μm) by the end of the sequence, i.e. at time $t_s=N \times t_{sep}$.

b) CHEMICAL MODEL OF NON-ABLATIVE RESURFACING

Typically, tissue damage response is calculated using the Arrhenius damage integral $\Omega$ calculated over the time ($t_{exp}$) of the temporally square-shaped thermal exposure to elevated temperature:

$$\Omega = A \exp(-E/RT) \times t_{exp}. \qquad (1)$$

Here, A is the frequency factor, i.e. the damage rate (in $s^{-1}$), E is the activation energy [in J/kmol], and R is the gas constant (R=8.31 $10^3$ J/kmol K). The damage integral defines the probability (P) for tissue damage response according to:

$$P = 1 - \exp(-\Omega). \qquad (2)$$

Similarly, the critical (i.e., damage threshold) temperature ($T_{crit}$), depends on the thermal exposure time as:

$$T_{crit} = E/(R \ln(A\ t_{exp})). \qquad (3)$$

During Er:YAG laser pulsing, the superficial tissue's thermal exposure transitions from intense, extremely short periods of exposure to peak temperatures $T_{max-i}$ (see FIG. 1A), to long-duration periods of exposure to moderate temperatures ($T \leq T_s$). For this reason, a two-process response model (hereinafter referred to also as the "VHS" model) can be used in order to evaluate the tissue damage $\Omega$ from the calculated temporal and spatial temperature profiles. The VHS model assumes that the effective damage integral $\Omega$ can be calculated for any exposure from the combined effect of the damage integrals $\Omega_{long}(t_{esp})$ and $\Omega_{short}(t_{exp})$ belonging respectively to the long and short Arrhenius processes (See FIG. 2), as follows:

$$(1/\Omega)^p = (1/\Omega_{long})^p + (1/\Omega_{short})^p. \quad (4)$$

where $p \approx 0.15$ is the transition coefficient that determines the transition between the two limiting biochemical processes. The details of the VHS model are described in [3].

The long and short processes are characterized by the following Arrhenius parameters: $A_{long} = 4.7 \times 10^{89}$ s$^{-1}$ and $E_{long} = 5.67 \times 10^7$ Jkmol$^{-1}$ for the long exposure process, and $A_{short} = 1.45 \times 10^4$ s$^{-1}$ and $E_{short} = 1.03 \times 10^7$ Jkmol$^{-1}$ for the short exposure process. Eq. (4) defines an implicit function of the critical temperature, i.e. at which $\Omega = 1$, depending on the exposure time, and is depicted in FIG. 2. For example, critical temperatures of approximately 70° C., 80° C., 90° C., 100° C., 110° C., 120° C., 160° C., 180° C., and 250° C. are obtained for thermal exposure times $t_{exp} = 150$ ms, 25 ms, 20 ms, 6 ms, 4.5 ms, 3.5 ms, 2 ms, 1.5 ms and 0.8 ms.

In some examples, the exposure time may be approximated by $t_{exp} = t_{ed} + (1/D)(\delta + \sqrt{(2 D t_{ed})})^2$, wherein D is the thermal diffusivity of the treated tissue which may be, for the aspects disclosed herein, approximated by $=0.1$ mm$^2$/s. $t_{ed}$ denotes the time during which the second half of the pulse energy is delivered (e.g. for temporally symmetric pulses $t_{ed} = t_p/2$). $\delta$ is the penetration depth in the target tissue which may depend on the wavelength of the pulse (sequence). For example, for Er:YAG lasers with a wavelength $\lambda$ 2,940 nm, $\delta \approx 1$ μm. For $CO_2$ lasers with wavelength $\lambda \approx 10,640$ nm, $\delta \approx 15$ μm. For example, for Er,Cr:YSGG lasers with $\lambda \approx 2,780$ nm, $\delta \approx 3$ μm.

The damage integral extending deeper into the tissue, characterized predominantly by the long-pulse exposure process, was calculated by integrating the damage over temperature instead of over time, using the algorithm developed for calculating tissue damage for temporally non-square-shaped thermal exposure pulses [3]. The tissue coagulation depth ($z_c$) was defined as the tissue depth below which the calculated cell injury is smaller than $\Omega = 0.5$.

It has been shown that the superficial tissue damage caused by a single Er:YAG laser pulse is governed mainly by the short-pulse Arrhenius process, and extends about $z_{1/2} \approx 10$ μm deep into the tissue. For calculating the cumulative short-pulse Arrhenius process damage to this superficial tissue layer, following a series of $i = 1 \ldots N$, intense short-duration thermal exposures to $T_{max-i}$, a probability-summation model was used similar to that in [5: Menendez A R, Cheney F E, Zuclich J A, Crump P. Probability-summation model of multiple laser-exposure effects. Health Phys 1993; 65:523-528]. In this model, it is assumed that the response to each pulse of a multiple-pulse exposure is independent of the response to other pulses; that is, previous pulses do not "sensitize" the tissue to subsequent pulses. The probability $P_i$ of thermal damage caused by each pulse, $i = 1 \ldots N$ is then calculated from $$P_i = 1 - \exp(-\Omega_i), \quad (5)$$

where $\Omega_i$ was calculated using Eqs. 1 and 4, assuming an exposure to a constant temperature $T_{max-i}$ for an effective duration $t_{eff}$. The effective duration was approximated by $t_{eff} \approx 0.25$ ms, based on results of simulations in [3], assuming $t_p = 0.3$ ms, and represented the duration of an imaginary rectangular temperature pulse of a constant average temperature $T_{maxi-}$, which produces approximately the same amount of damage as the actual "triangularly" shaped temperature pulse. The cumulative "sequence" probability $P_s$ (N) of inducing a thermal damage to the tissue surface during N pulses was then calculated using:

$$P_s(N) = 1 - (1 - P_1)(1 - P_2) \ldots (1 - P_N). \quad (6)$$

This gives an approximate cumulative damage integral averaged over the $z_{1/2} \approx 10$ μm thick thermally affected superficial layer as:

$$\Omega(N) = 0.5 \times \text{Ln}(1/(1 - P_s(N))). \quad (7)$$

It is to be noted that although $T_{max-i}$ temperatures were calculated taking into account the gradual temperature increase during the pulse sequence, the above damage does not include the longer exposure tissue response resulting from this gradual temperature build-up.

c) HEAT-PAIN THRESHOLD MEASUREMENT

In order to determine the heat-pain threshold (HPT) for different smooth-resurfacing conditions, 15 patients participated in the experiment on a voluntary basis. Thermal stimuli were delivered using an Er:YAG laser (Dynamis SP, manufactured by Fotona d.o.o.; operating in a V-SMOOTH pulse mode). Sequences with pulse separation times $t_{sep} = 25$, 100, and 125 ms were applied, with pulse numbers up to $N = 36$. The laser pulse duration was equal to $t_p = 0.3$ ms. The laser energy was delivered to the abdominal skin area using a T-Runner scanning handpiece (manufactured by Fotona d.o.o.) with a single full-beam spot size of $2r = 9$ mm, scanned over a scanning area consisting of $3 \times 3$ spots. Heat-pain thresholds were obtained for treatments without and with topical anesthesia (application of EMLA 25 minutes before the test).

The cumulative laser fluence was gradually increased for each successive scan in steps of 0.2 J/cm$^2$ from a low level until the patient characterized the treatment pain as intolerable. The pain threshold can be understood as the fluence just below the value at which the patient reported the discomfort during the treatment to be unacceptable.

d) TISSUE SURFACE TEMPERATURE MEASUREMENT

Measurements of the tissue surface temperature evolution as a result of Er:YAG laser irradiation were made on the abdominal skin and on mucosa (intraorally on the cheeks) using the Dynamis SP laser system (manufactured by Fotona d.o.o.) operating in SP pulse duration mode ($t_p = 0.3$ ms). In what follows it will be assumed that the data for the intra-oral tissue represents all mucous tissues, including the vaginal tissue.

For measuring the temporal temperature profile during longer-duration pulse stacking, a thermal camera (ThermaCAM P45, manufactured by FUR Systems, USA) with a frame rate of 50 Hz was used. Two laser handpieces were used: i) a full-beam handpiece (Fotona R11) and ii) a pixelated beam handpiece (Fotona PS03), with both handpieces set to a 7 mm spotsize. The Fotona PS03 handpiece is equipped with a pixel screen, resulting in the overall laser spot having a pixelated (also referred to as patterned or dotted) internal beam structure, with the centers of the individual circular beam dots of diameter of $2r = 0.85$ mm being separated by approximately 2 mm center to center. The motivation behind the design of the pixelated PS03 handpiece is to make the treatment less invasive by reducing the treatment area to isolated beam islands.

e) RESULTS aa) Single Pulse Exposure

As can be seen from FIG. 1A, each individual temperature pulse (i) consists of the temperature ramp-up heating phase during which the temperature reaches its maximal value ($T_{max-i}$), and (ii) of the cooling phase during which the temperature returns back to its initial temperature ($T_{oi}$). The heating phase lasts for approximately the duration of the laser intensity pulse ($t_p$), while the cooling phase is determined predominantly by the rate of the heat flow away from the heated superficial tissue.

For fluences below the ablation threshold, the peak tissue temperature $T_{max}$ grows linearly with fluence at the single pulse temperature slope $\eta_p = \Delta T_{max}/F_p$, where $\Delta T_{max} = T_{max} - T_o$. The peak temperature increases with laser pulse fluence ($F_p$) until the ablation threshold is reached, at which point the peak temperature reaches the ablation ("boiling") temperature $F_p = F_{abl}$.

FIG. 2 presents the influence of the single-pulse duration $t_p$ (ms) on the temperature slope $\eta_p$ (° C. cm²/J) and on the ablation threshold fluence $F_{abl}$ (J/cm²). The initial temperature was taken to be equal to $T_o = 35°$ C. The fits to the data points shown in FIG. 2 represent the dependence of the single-pulse temperature slope $\eta_p$ (in ° C. cm²/J), and of the single-pulse ablation threshold fluence $F_{abl}$ (in J/cm²) on the single full-beam laser pulse duration $t_p$ (in ms) based on the following equations:

$$\eta_p \approx A_p \times t_p^{-Kp}, \quad (8)$$

and $$F_{abl} \approx A_F \times t_p^{Kp}, \quad (9)$$

where $K_p = 1/3$, and the full-beam values for skin are $A_p = 173$ and $A_F = 1.28$. The corresponding estimated full-beam values for mucosa (such as, for example, vaginal and oral mucous tissue) are $A_p = 144$ and $A_F = 1.5$. The corresponding values for the patterned beam are $A_p = 81$ and $A_F = 2.7$ for skin, and $A_p = 67$ and $A_F = 3.3$ for mucosa.

For fluences above $F_{abl}$, the peak temperature remains fixed at $T_{abl}$ by means of micro-explosions, similarly to the case of boiling water that keeps its temperature at about 100° C. regardless of the heating power. Using our numerical model, the soft-tissue ablation temperature is calculated to be $T_{abl} = 256 \pm 10°$ C., regardless of pulse duration. It is to Be noted that the relationship between the parameters $A_p$ and $A_F$ in Eqs. 8 and 9 above is then according to $A_F = (256° C. - 35° C.)/A_p$.

bb) Multiple Pulse Exposure

Our simulations show that for fluences below the ablation threshold, the sequence temperature increase $\Delta T_s = T_s - T_o$ is linearly dependent on $F_s$:

$$\Delta T_s \approx \eta_s \times F_s, \quad (10a)$$

where $\eta_s = \Delta T_s / F_s$ is the sequence temperature slope for a particular set of sequence parameters. While the dependence of the sequence temperature slope on the single-pulse duration ($t_p$) or on the number of pulses N is relatively small (and may be neglected), the dependence of the slope $\eta_s$ (in units of ° C. cm²/J) on the sequence duration $t_s$ (in msec), as obtained by fitting the numerical results to a power function, was found to be well described by:

$$\eta_s = A_s t_s^{Ks}. \quad (10)$$

Here, the coefficients for the full beam treatments of the skin are $A_s = 84$ and $K_s = -0.43$. Using these parameters, the numerically predicted dependence of $\eta_s$ on $t_s$ is in FIG. 4 represented by the upper full line. As can be seen from FIG. 4, the simulated dependence is in a good agreement with the slopes as measured for the full beam treatment of the abdominal skin (depicted by full circles).

Additionally, FIG. 4 shows the measured slopes for the full beam treatment of the mucous tissue, together with the fit of the experimental data to Eq. 10 with the coefficients $K_s = -0.43$, and $A_s = 69$ (represented by the lower full line). Similarly, dotted lines represent fits of the experimental data to Eq. 10 for a patterned handpiece (i.e., Fotona PS03), with the coefficients $K_s = -0.43$, and $A_s = 28$ for the patterned beam treatment of skin and $A_s = 18$ for the patterned beam treatment of mucosa. The difference between coefficients for skin and mucosa is attributed to the fact that the moist mucous tissue requires slightly more energy than the dry skin to be heated up. The lower coefficients for the patterned handpiece as compared with coefficients for the full beam handpiece are attributed to the radial heat diffusion away from the micro spots, in addition to the heat diffusion deeper into the tissue.

The obtained single pulse and sequence temperature slopes are used in further analysis to calculate the sequence ablation thresholds ($F_{thr}$) as follows. The sequence ablation threshold is first reached when the maximal temperature ($T_{max-N}$) of the last pulse (i=N) in the sequence with duration $t_s$ reaches the ablation temperature $T_{abl}$. Assuming that all laser pulses (i=1 ... N) in the sequence have the same fluence $F_p$, then ablation starts when $\Delta T_{s-N-1}(N-1) + \eta_p F_p = \Delta T_{abl} = 256°$ C. $- T_o = 221°$ C., where $\Delta T_{s-N-1}$ is the temperature elevation for the pulse sequence with N-1 pulses, and correspondingly with the pulse sequence duration equal to $t_s(N-1)/N$. The ablation threshold fluence for any pulse sequence $F_{thr} = N \times F_p$ (in J/cm²) can then be calculated from:

$$F_{thr} = N \Delta Tabl(\eta_P(t_p) + (N-1)\eta_s(t_s(N-1)/N))^{-1} \quad (11)$$

Analysis of Eq. 11 shows that the sequence ablation threshold depends more strongly on N and $t_p$, and less on $t_s$, especially for longer $t_s$.

cc) Pain Threshold Fluences

FIG. 5A shows cumulative pain threshold fluences $F_{pain}$ (J/cm²), as obtained for treatments without topical anesthesia on 15 patients for four pulse sequence settings: i) N=6, $t_s$=150 ms; ii) N=30, $t_s$=3750 ms; iii) N=36, $t_s$=3600 ms; and iv) N=36, $t_s$=4500 ms. As can be seen from FIG. 6A, while pain thresholds vary from patient to patient, the pain threshold fluence is generally higher for longer sequence duration $t_s$.

Figure 5B:
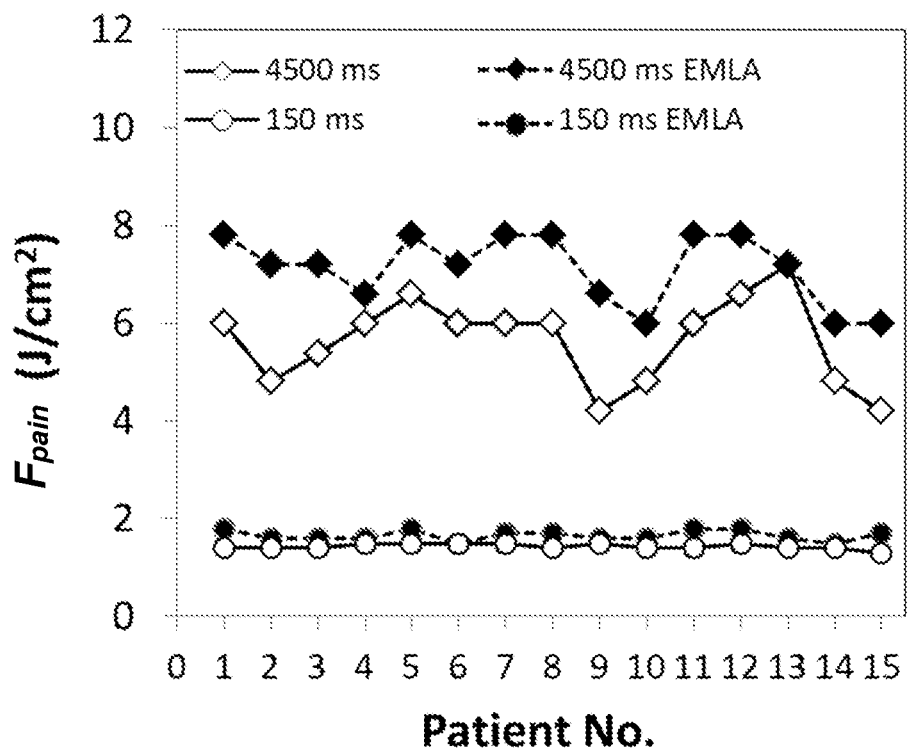

FIG. 5B shows pain threshold fluences $F_{pain}$ (J/cm²), as obtained for treatments with (closed symbols) and without (open symbols) topical anesthesia for sequence durations $t_s$=150 ms and 4500 ms. Also FIG. 5B confirms the difference in pain threshold fluences for two sequence durations (150 ms and 4500 ms), and also shows their dependence on whether topical anesthesia (EMLA cream) was used or not.

Assuming that pain is associated mainly with the overall sequence temperature $T_s$, and not with short-duration maximal temperatures $T_{max-i}$, then the pain threshold temperatures ($T_p$) can be obtained by calculating sequence temperatures at the measured pain fluences $F_{pain}$, using Eq. 10.

The resulting pain threshold elevation $\Delta T_p = T_p - T_o$ (° C.) obtained for treatments without anesthesia, for sequence times $t_s$=150, 3600, 3750 and 4500 ms is on average $\Delta T_p$=12.7 OC. Average pain threshold temperatures for treatments without (averaged over 150, 3600, 3750 and 4500 ms data) and with topical anesthesia (averaged over 150 and 4500 ms data) were $\Delta T_p=12.7°$ C., and with anesthesia, $\Delta T_{p\text{-}EMLA}=16.1°$ C.

Figure 6B:
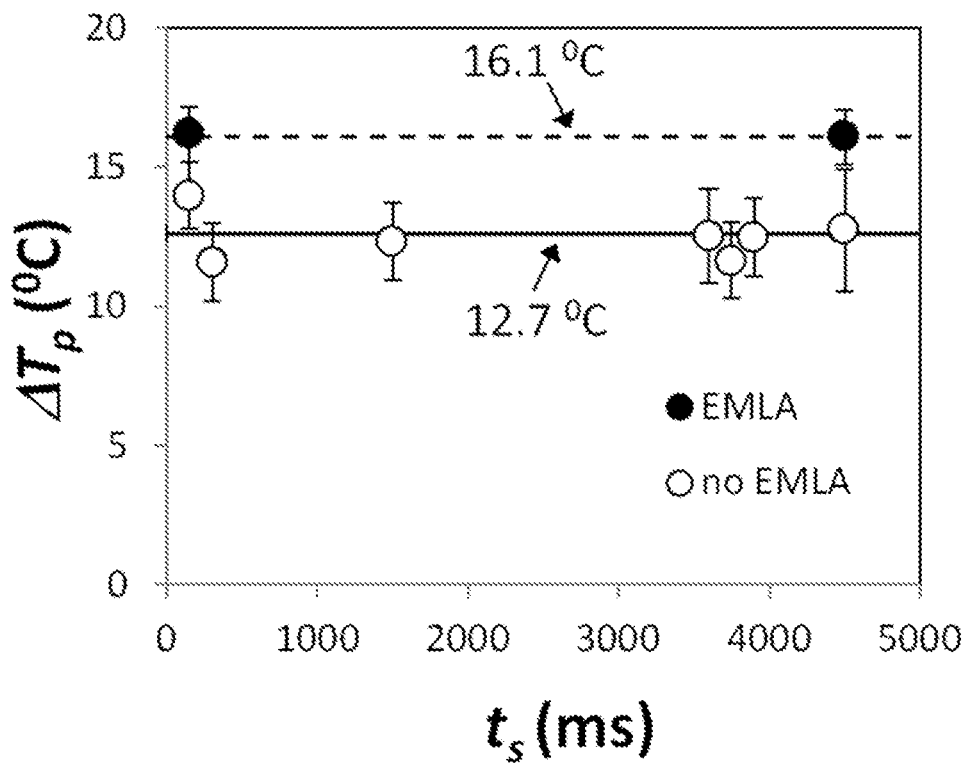

FIGS. 6A and 6B show the dependence of the measured pain threshold fluence $F_{pain}$ on the sequence duration $t_s$, averaged over the 15 patients' data (FIG. 6A), and of the corresponding calculated pain threshold temperature elevations (FIG. 6B), with (closed symbols) and without (open symbols) topical anesthesia. The lines in FIG. 6A represent calculated pain thresholds according to Eq. 10, with $\Delta T_p=12.7°$ C. without (dashed line), and $\Delta T_{p\text{-}EMLA}=16.1°$ C. with topical anesthesia (full line). The fit to the data points is better than $R^2=0.98$. As can be seen from FIG. 6B, the calculated pain threshold temperature represented by the sequence temperature is found to be approximately constant over a large range of sequence durations. On average, the pain threshold temperature elevation is equal to $\Delta T_p=12.7\pm2.0°$ C. for treatments without anesthesia, and to $\Delta T_{p\text{-}EMLA}=16.1\pm2°$ C. for treatments with topical anesthesia.

It is to be noted that the above pain thresholds were measured on the abdominal skin. Typically, cutaneous heat pain threshold temperatures (HPTT) for several-seconds-long exposures are for different body areas in the range of 41-52° C., in rough agreement with the pain threshold temperature for smooth-resurfacing of abdominal skin of $T_p$ 48° C., as found in our experiments. In agreement with the VHS model and the assumption that the pain threshold is related to the risk of irreversible damage, the HPTT has been observed to increase towards shorter exposures, and was reported to be equal to HPTT≈58° C. for $t_{exp}$≈0.3 s and to HPTT≈75° C. for $t_{exp}$≈0.05 s. Similar heat pain thresholds have also been obtained for oral mucosa, with HPTT≈48° C. for long exposures, and HPTT≈65-70° C. for approximately 0.1 s long exposures.

dd) Deep Tissue Response

FIG. 7 shows calculated coagulation depths $z_c$ (μm) as a function of the sequence duration $t_s$ (ms), for different sequence durations when smooth-resurfacing is performed, i.e. when the sequence fluence is for each sequence duration adjusted to be just below the pain threshold $F_{pain}$ or $F_{pain\text{-}EMLA}$ (abbreviated as $F_p$ or $F_{p\text{-}EMLA}$ in FIG. 7), for treatments without or with topical anesthesia, respectively ($t_{sep}=25$ ms (diamonds), 75 ms (squares) and 125 ms (circles)).

The pain threshold fluences were calculated using Eq. 10 for $\Delta T_p=12.7°$ C. (without anesthesia) and 16.1° C. (with topical anesthesia) according to $F_{pain}=\Delta T_p/\eta s$. As can be concluded from FIG. 7 (full lines), smooth-resurfacing can result in significant coagulation depths, providing that appropriately long sequence durations is are used, which allow sufficiently high yet still painless sequence fluences $F_s$. For example, when using topical anesthesia, the pain threshold fluence at $t_s=10$ S is equal to $F_{pain\text{-}EMLA}≈10$ J/cm². Also, based on our finding, the coagulation depths at the "smooth" fluences, i.e., at the fluences just below the pain threshold, do not depend on the number of pulses N nor on the pulse separation time $t_{sep}$, but are determined solely by the sequence duration $t_s$. Hence, methods and apparatus may be provided based on this insight, that take this into account and provide means for user-based and/or (programmed) to automatic settings accordingly, e.g. applying a sequence with a predetermined pulse sequence duration to achieve a predetermined coagulation depth. For example, a user interface may be provided such that an operator of a corresponding device may select a certain coagulation depth and/or a skin type (e.g. anesthetized or non-anesthetized skin). The device may then automatically apply a laser pulse sequence with a corresponding required cumulative fluence and corresponding pulse duration. In other examples, a user may be displayed (information on the expected) coagulation depth for a setting.

ee) Superficial Tissue Response

Figure 8B:
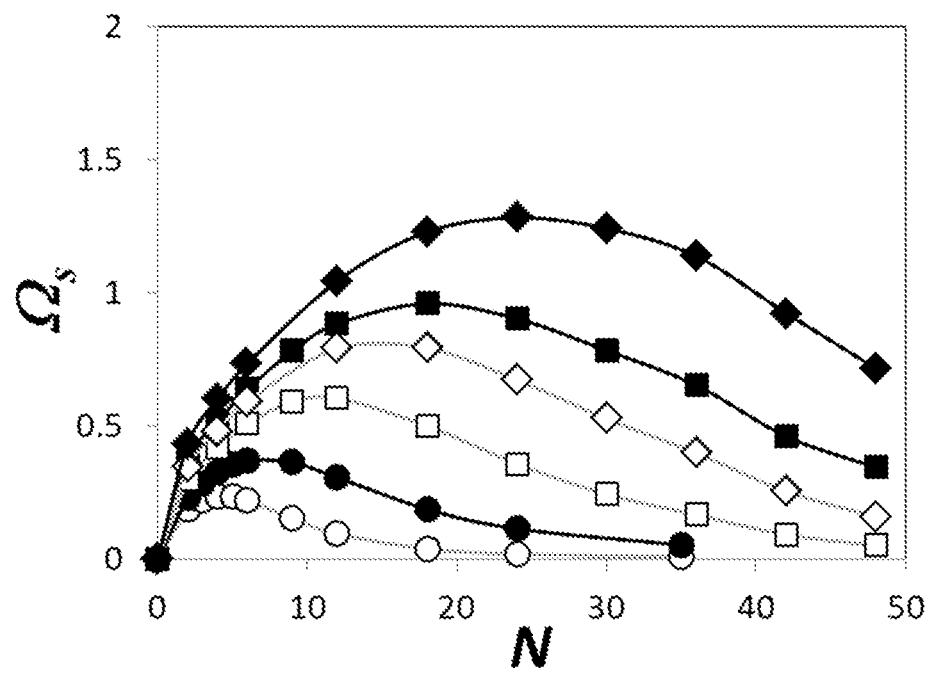

FIGS. 8A and 8B show the calculated short-exposure superficial damage ($\Omega_s$) for smooth-resurfacing (black and open symbols connected by full lines) applications, as a function of the sequence duration $t_s$ (FIG. 8A) or number of pulses N (FIG. 8B), as calculated using Eq. 7. Black and open symbols represent smooth-resurfacing with and without topical anesthesia, respectively. The calculated damage integrals are for pulse separation times $t_{sep}$ of 25 ms (diamonds), 85 ms (squares) and 125 ms (circles).

As can be seen from FIGS. 8A and 8B, using the smooth-resurfacing technique as described herein may represent a significant advantage since the damage can be limited to a maximal level defined by the number of pulses N and pulse sequence duration $t_s$ (or alternatively by the pulse separation time $t_{sep}=t_s/N$).

In this invention, the level of superficial heat shock triggering is evaluated by assuming that the level of thermal "needling" is related to the superficial damage resulting from the multiple short-duration exposures. The superficial heat shocking resembles the effects of the micro-needling technique, which aims not to injure keratinocytes but to stimulate them with superficial punctures and without any injury to fibroblasts. The smooth-resurfacing laser-induced thermal triggering mechanism can be viewed as non-ablative thermal "needling" (i.e., triggering) of the total treated skin surface, with the action of the spatially sharp needles being replaced by the action of temporarily "sharp" but spatially extended heat shock pulses.

f) DISCUSSION

During an Er:YAG laser pulse sequence, the laser-generated heat dynamics exhibits two phenomena: i) intense short-duration thermal pulses resulting from individual laser pulses i, with peak temperatures ($T_{max\text{-}i}$) at the surface that may exceed 200° C. (see FIG. 1A), biochemically directly affecting only the approximately 10 μm deep superficial tissue layer; and ii) a slow gradual build-up of the spatial temperature distribution over the total duration of the sequence, extending several hundred microns deep into the tissue, with the surface temperatures ($T_s$) typically below 50-70° C. (see FIG. 1B).

Similarly, based on FIGS. 7, 8A and 8B, it can be concluded that for the smooth-resurfacing as described herein, there are two optimal treatment regimes.

When a maximal heat shock triggering effect, with optimal short exposure damage $\Omega$, and moderate coagulation depths of about 100 μm are desired, the optimal sequence durations and number of pulses are in the range up of about $t_s=1-3$ s (See FIG. 8A) and N=12-30 pulses, or N=12-24 pulses (See FIG. 8B). An exemplary set of protocols for full beam superficial triggering of skin is depicted in Table 1 below. For example, without anesthesia, N=10-20, or 10-18 or about 12 may be preferable. For anesthesia N=10-30, or 15-25 or about 24 may be preferable.

TABLE 1

| Sequence duration, $t_s$ | ms | Without topical anesthesia | | | | |
|---|---|---|---|---|---|---|
| | | 150 | 300 | 900 | 1200 | 1500 |
| Fluence, $F_s$ | J/cm² | 1.3 | 1.7 | 2.8 | 3.2 | 3.4 |
| Pulse number, N | / | 6 | 6 | 12 | 12 | 12 |
| $\Delta T_s/\Delta T_p$ | % | 92 | 90 | 92 | 93 | 90 |
| Coagulation depth, $z_c$ | µm | 64 | 68 | 71 | 72 | 66 |
| Superficial $\Omega_s$ | / | 0.22 | 0.37 | 0.53 | 0.69 | 0.82 |

| Sequence duration, $t_s$ | ms | With topical anesthesia | | | | |
|---|---|---|---|---|---|---|
| | | 150 | 600 | 1350 | 1800 | 3000 |
| Fluence, $F_s$ | J/cm² | 1.6 | 3.0 | 4.2 | 4.8 | 6.0 |
| Pulse number, N | / | 6 | 12 | 18 | 24 | 24 |
| $\Delta T_s/\Delta T_{p\text{-}EMLA}$ | % | 114 | 117 | 116 | 117 | 118 |
| Coagulation depth, $z_c$ | µm | 82 | 109 | 121 | 133 | 162 |
| Superficial $\Omega_s$ | / | 0.35 | 0.64 | 0.84 | 1.07 | 1.29 |

And when deeper coagulation depths are to be achieved, then long sequence durations of about $t_s$=5-10 s (See FIG. 7), consisting of a large number of pulses of about N=80-150, are to be used. Under these deep coagulation conditions, the heat shock triggering effect is extremely small, typically below $\Omega_s 2$=0.05. An exemplary set of protocols for full beam deep coagulation of skin is depicted in Table 2 below.

TABLE 2

| Sequence duration, $t_s$ | ms | Without topical anesthesia | | | | |
|---|---|---|---|---|---|---|
| | | 1200 | 4200 | 8100 | 13800 | 20250 |
| Fluence, $F_s$ | J/cm² | 3.2 | 5.6 | 7.2 | 9.2 | 10.8 |
| Pulse number, N | / | 48 | 84 | 108 | 138 | 162 |
| $\Delta T_s/\Delta T_p$ | % | 93 | 95 | 92 | 94 | 93 |
| Coagulation depth, $z_c$ | µm | 72 | 93 | 117 | 199 | 295 |
| Superficial $\Omega_s$ | / | 0.0025 | 0.0049 | 0.0056 | 0.0076 | 0.0087 |

| Sequence duration, $t_s$ | ms | With topical anesthesia | | | | |
|---|---|---|---|---|---|---|
| | | 1800 | 6000 | 12600 | 20400 | 30000 |
| Fluence, $F_s$ | J/cm² | 4.8 | 8.0 | 11.2 | 13.6 | 24.0 |
| Pulse number, N | / | 72 | 120 | 168 | 204 | 240 |
| $\Delta T_s/\Delta T_{p\text{-}EMLA}$ | % | 117 | 116 | 118 | 117 | 117 |
| Coagulation depth, $z_c$ | µm | 133 | 236 | 461 | 674 | 909 |
| Superficial $\Omega_s$ | / | 0.0095 | 0.0155 | 0.0234 | 0.0270 | 0.0313 |

In some examples, the apparatus as described herein may be implemented to provide a pulse sequence with N=100 to 220 pulses and a cumulative fluence of about 7 to 15 J/cm² (without anesthesia). In some examples, the apparatus as described herein may be implemented to provide a pulse sequence with N=150 to 250 pulses and a cumulative fluence of about 10 to 25 J/cm² (with anesthesia). The sequence duration may be about 0.8 to 1.2 times that required to reach the pain threshold temperature as defined herein.

The apparatus as described herein may comprise a pre-calibrated mode to which a user may switch that provides one or more of the above pulse sequences, e.g., for superficial triggering and/or deep coagulation.

Therefore, when the patient's pain tolerance is used as the treatment safety criteria for selecting appropriate laser parameters, the above heat dynamics leads to two distinct treatment protocol regimens: i) the optimal superficial triggering regimen, represented by Table 1; and ii) the optimal direct stimulation and coagulation regimen, represented by Table 2. In conclusion, based on the analysis and taking in consideration also the treatment duration, the following three full beam smooth-resurfacing treatment embodiments are preferred:

aa) INTENSE smooth-resurfacing protocol for maximal superficial heat shock triggering with exemplary protocol parameters according to Table 1 for superficial $\Omega_s$=0.82 and $\Omega_s$=1.29 for treatments without and with topical anesthesia, correspondingly.

For example, a pulse sequence with 10 to 35 (or 12 to 30) pulses during a sequence duration 300 to 3000 ms (or 1000 to 2500 ms) may be used, having a cumulative fluence of 3 J/cm² to 8 J/cm². The apparatus as described herein may comprise a pre-calibrated mode to which a user may switch that provides such a pulse sequence, e.g. with a pulse duration depending on the skin type.

bb) HYPERSTACK smooth-resurfacing protocol for maximal deep thermal stimulation, with exemplary protocol parameters according to Table 2 for coagulation depth $z_c$=296 µm and $z_c$=480 µm for treatments without and with topical anesthesia, accordingly. For example, a pulse sequence with 100 to 400 (or 200 to 300 or 100 to 200) pulses during a sequence duration of 6000-40000 ms (or 8000 to 20000 ms) may be used, having a cumulative fluence of 8 J/cm² to 14 J/cm². The apparatus as described herein may comprise a pre-calibrated mode to which a user may switch that provides such a pulse sequence, e.g. with a pulse duration depending on the skin type.

cc) DUAL smooth-resurfacing protocol for when it is desired to achieve both, superficial triggering and deep thermal stimulation effects within a single procedure.

For example, a pulse sequence with 40 to 90 pulses during a sequence duration of 600-12000 ms may be used, having a cumulative fluence of 7 J/cm$^2$ to 12 J/cm$^2$. The apparatus as described herein may comprise a pre-calibrated mode to which a user may switch that provides such a pulse sequence, e.g. with a pulse duration depending on the skin type.

Our analysis also shows that patterned handpieces may be better suited for the maximal heat shock triggering effect procedures compared to full beam handpieces. Hence, it may be beneficial to use a pixelated beam. For this reason, according to one of the preferred embodiments of present invention, the energy is delivered to the tissue in a "patterned" shape, wherein the laser beam irradiates a number (M) of individual spots S within the treatment area S'. Each spot S having the size (e.g., diameter) d is separated from a neighbouring spot by the distance x (see FIG. 9). The spot size d and the distance x are chosen such that the spot size d is in the range of 0.3 mm≤d≤1.5 mm, and that the tissue coverage $T_C$=(M×area(S))/area(S') (in %) is in the range of 25%≤$T_C$≤65%. Further, the size (e.g., diameter) of the treatment area S' which comprise all the spots is in the range of 3 to 15 mm. These parameters ensure that, during the sequence duration $t_s$ the thermal diffusion in the lateral direction spreads the heat which is generated by the laser radiation away from a localized spot S towards the surroundings of the spot, thus effectively spatially homogenizing the temperature $T_s$ across the area S', while at the same time the spotsize d is large enough to enable the pulse fluence $F_p$ to be set to a required value being below the ablation threshold $F_{abl}$.

Namely, with patterned handpieces. the irradiated tissue does not cool down only by the heat diffusion deeper into the tissue but also by the heat diffusion in the radial direction away from the irradiated microspots. This cooling mechanism is more effective during the long sequence duration ($t_s$) than during the short duration temperature peaks. For this reason, the final sequence temperature ($T_a$) is more significantly reduced than the temperature peaks $T_{max-i}$. As can be seen from FIG. 4, the temperature slope coefficient $A_s$ is for a patterned handpiece by a factor of 3-4 smaller as compared to the slope for the full beam handpiece (See Eq. 7). This means that 3-4 times higher cumulative fluences ($F_s$) can be delivered without exceeding the pain tolerance threshold temperature. On the other hand, since the radial heat diffusion has a smaller effect on the high temperature peaks ($T_{max-i}$), the higher cumulative fluence will for the same level of deep tissue coagulation result in an increased level of superficial triggering. Therefore, patterned handpieces are generally better suited for the maximal heat shock triggering effect compared to full beam handpieces.

To demonstrate the influence of radial heat diffusion for small diameter beam sizes we carried out a limited numerical analysis using a 3D cylindrical coordinate system model. The resulting temporal profiles of the skin surface temperature during a sequence with N=24 micro pulses, delivered by a full beam ((R11 with 7 mm spotsize) or by a patterned beam handpiece (PS03 with 0.85 mm micro spotsize) are shown in FIGS. 10A and 10B. FIGS. 10A and 10B show calculated temporal profile of the skin surface temperature during a sequence of four SMOOTH mode macro pulses each consisting of 6 micro pulses (resulting in N=4×6=24 micro pulses) for $F_s$=4.9 J/cm2 with a full beam handpiece (R11 with 7 mm spotsize) (FIG. 10A); and b) $F_s$=14.7 J/cm2 with a patterned beam handpiece (PS03 with 0.85 mm micro spotsize) (FIG. 10B).

As can be seen from FIGS. 10A and 10B, for the same final sequence temperature ($T_s$=60° C.) (and resulting deep tissue response), the high temperature peaks ($T_{max-i}$) are approximately 30% higher for the patterned handpiece. A damage integral calculation using Eqs. 5 and 6 shows that this difference results in 2 times stronger (in terms of Ω) patterned thermal "needling" of the tissue.

g) CONCLUSIONS

In conclusion, Er:YAG laser pulse stacking represents an example of complex thermal exposure dynamics during which the exposure times transition from extremely short to long durations. The tissue effects resulting from these dynamics were evaluated numerically using the VHS model, for two examples of non-ablative or minimally ablative Er:YAG laser pulse stacking treatments: i) the "sub-resurfacing" performed at or near ablation laser fluences; and ii) the "smooth-resurfacing" characterized by below-pain-threshold fluences.

Based on measurements on abdominal skin, the pain threshold temperature depends mainly on the long-exposure superficial skin temperature ($T_s$) by the end of the pulse sequence, and not on the peak skin temperatures ($T_{max}$) following individual laser pulses within the sequence.

Our simulations show that for sub-resurfacing (i.e., resurfacing with fluences at or just below the ablation threshold fluence), the parameter range where no excessive damage to the tissue can occur is very narrow. On the other hand, using pain tolerance as an indicator, the smooth-resurfacing treatments can be performed more safely and without sacrificing the treatment efficacy.

Two preferred smooth (non-ablative) resurfacing treatment modalities were identified. One involves using optimally long pulse sequence durations (≈1-3 s) with an optimal number of pulses (N≈10-30), resulting in a maximal short-exposure superficial tissue response and moderate coagulation depths. And for deeper coagulation, without significant superficial heat shocking, very long pulse sequences (>5 s) with a large number of delivered pulses are to be used (preferably in combination with topical anesthesia).

h) EXEMPLARY EMBODIMENT

FIG. 11 shows an exemplary embodiment 100 of an apparatus according to the present invention. It may comprise a user interface 110, a control unit 120 and a laser source 130, e.g. as described herein. User interface 110 may receive one or more selection inputs and/or parameters. Based thereon, selection inputs and/or parameters may be provided to control unit 120. Control unit 120 may control laser source 130 accordingly to provide one or more laser pulse sequences as described herein. Control unit 120 may include a computer and/or processor and a memory. The memory may comprise one or more computer programs stored thereon as described herein.

The invention claimed is:

1. Apparatus for generating a laser pulse sequence for application to a predetermined target tissue, comprising:
means for setting a cumulative fluence $F_s$ of the laser pulse sequence;

means for determining a duration of the laser pulse sequence as a function of the cumulative fluence $F_s$ such that the predetermined target tissue is heated to a final temperature that is within a predetermined range;

wherein the means for determining is adapted to determine the duration based on a temperature model for the final temperature, wherein the temperature model is a function of the duration and the cumulative fluence $F_s$.

2. Apparatus according to claim 1, wherein the means for determining is adapted to determine the duration such that the final temperature is below a predetermined pain threshold temperature specific for the predetermined target tissue.

3. Apparatus according to claim 1, wherein the laser pulse sequence has a predetermined number N of sequential pulses, and the means for determining is adapted to determine the duration such that the final temperature at time $t_s = N \times \Delta t$ after application of the first pulse of the pulse sequence is within the predetermined range, wherein $\Delta t$ represents an average separation time between subsequent pulses of the pulse sequence.

4. Apparatus according to claim 1, further comprising:
means for setting at least one parameter indicative of the predetermined target tissue;
wherein the means for determining are adapted to determine the duration based on the at least one parameter.

5. Apparatus according to claim 1, further comprising:
means for generating the laser pulse sequence with the determined duration; and/or
means for receiving a setting of the duration of the laser pulse sequence and means for issuing a warning if the setting of the duration deviates from the determined duration by a predetermined threshold.

6. Apparatus according to claim 1, the apparatus further comprising:
at least two predetermined modes for generating the laser pulse sequence between which can be switched;
pre-calibrated means for generating the laser pulses of the laser pulse sequence with an average pulse fluence $F_{ave} = (F_1 + \ldots + F_N)/N$ of the pulse sequence, such that a mean value of maximum temperature increases of the predetermined target tissue caused by each of the individual pulses of the pulse sequence is within one of the following three ranges in the first mode and within a disparate one of the following three ranges in the second mode: 5° C. to 30° C.; 30° C. to 65° C.; 65° C. to 135° C.

7. Apparatus according to claim 1, further adapted such that:
the pulse sequence comprises between 6 and 40 pulses;
wherein the apparatus is adapted to apply the pulse sequence in a non-pixelated manner, and the cumulative fluence $F_s = F_1 + \ldots + F_N$ of the pulse sequence is between 2.5 and 8 J/cm²; or
wherein the apparatus is adapted to apply the pulse sequence in a pixelated manner, and the cumulative fluence $F_s = F_1 + \ldots + F_N$ of the pulse sequence is between 7.5 and 24 J/cm².

8. Apparatus according to claim 1, adapted to apply a first laser pulse sequence to a first position on the target tissue and a second laser pulse sequence to a second position on the target tissue;
wherein the apparatus further comprises a scanner;
wherein the scanner is adapted to automatically apply a first pulse of the second pulse sequence to the second position at a period of time after a first pulse of the first sequence has been applied to the first position, the period of time being the inverse of a maximum pulse generation frequency, but before a last pulse of the first sequence has been applied to the first position.

9. Apparatus according to claim 1, further adapted such that:
the pulse sequence comprises between 12 and 30 pulses;
wherein the apparatus is adapted to apply the pulse sequence in a non-pixelated manner, and the cumulative fluence $F_s = F1 + \ldots + FN$ of the pulse sequence is between 2.5 and 5 J/cm²; or
wherein the apparatus is adapted to apply the pulse sequence in a pixelated manner, and the cumulative fluence $F_s = F1 + \ldots + FN$ of the pulse sequence is between 7.5 and 15 J/cm².

10. Apparatus for generating a laser pulse sequence for application to a predetermined target tissue, comprising:
means for setting a duration $t_s$ of the laser pulse sequence;
means for determining a cumulative fluence $F_s$ of the laser pulse sequence as a function of the duration such that the predetermined target tissue is heated to a final temperature that is within a predetermined range;
wherein the means for determining is adapted to determine the duration based on a temperature model for the final temperature, wherein the temperature model is a function of the duration and the cumulative fluence $F_s$.

11. Apparatus according to claim 1, further comprising one or more user interfaces for receiving:
a selection input representative of the duration and/or the cumulative fluence of the laser pulse sequence; and/or
a selection input representative of a tissue type, and/or a selection input representative of a pixelization of the laser pulse sequence.

12. Apparatus according to claim 1, wherein the apparatus comprises an Er:YAG laser source for generating the laser pulse sequence and wherein the means for determining is adapted to determine the duration $t_s$ and/or the cumulative fluence $F_s$ of the pulse sequence such that $(1-x_1)\Delta T_p/(A_s \times t_s^{-Ks}) < F_s < (1+x_2)^* \Delta T_p/(A_s \times t_s^{-Ks})$, wherein $\Delta T_p$ is 22° C., $x_1 = 0.5$, $x_2 = 0.5$, $K_s = 0.43$; wherein $A_s$ is a predetermined parameter.

13. Apparatus according to claim 11, wherein the apparatus comprises an Er:YAG laser source for generating the laser pulse sequence and wherein the means for determining is adapted to determine the duration $t_s$ and/or the cumulative fluence $F_s$ of the pulse sequence such that $(1-x1)\Delta Tp/(As \times t_s - Ks) < F_s < (1+x2)^* \Delta Tp/(As \times t_s - Ks)$, wherein $\Delta Tp$ is 22° C., $x1 = 0.5$, $x2 = 0.5$, $Ks = 0.43$; wherein As is a predetermined parameter, and wherein:
$A_s = 84$ (° C. cm²)/J, if selection input according to claim 8 indicates human skin as tissue type and no pixelization of the laser pulse sequence; and/or
$A_s = 69$ (° C. cm²)/J, if selection input according to claim 8 indicate human mucosa as tissue type and no pixelization of the laser pulse sequence; and/or
$A_s = 28$ (° C. cm²)/J, if selection input according to claim 8 indicate human skin as tissue type and pixelization of the laser pulse sequence; and/or
$A_s = 18$ (° C. cm²)/J, if selection input according to claim 8 indicate human mucosa as tissue type and pixelization of the laser pulse sequence.

14. Method for generating a laser pulse sequence for application to a predetermined target tissue, comprising:
setting a cumulative fluence $F_s$ of the laser pulse sequence;
determining a duration of the laser pulse sequence as a function of the cumulative fluence such that the predetermined target tissue is heated to a final temperature that is within a predetermined range;

wherein determining the cumulative fluence is based on a temperature model for the final temperature, wherein the temperature model is a function of the duration and the cumulative fluence $F_s$.

15. Method for generating a laser pulse sequence for application to a predetermined target tissue, comprising:
setting a duration t of the laser pulse sequence;
determining a cumulative fluence $F_s$ of the laser pulse sequence as a function of the duration such that the predetermined target tissue is heated to a final temperature that is within a predetermined range;
wherein determining the cumulative fluence is based on a temperature model for the final temperature, wherein the temperature model is a function of the duration and the cumulative fluence $F_s$.

* * * * *